United States Patent
Johnston et al.

(10) Patent No.: US 10,449,247 B2
(45) Date of Patent: Oct. 22, 2019

(54) COMPOSITIONS AND METHODS FOR ENHANCING IMMUNE RESPONSE

(75) Inventors: James Johnston, Stratford (CA); Bozena Korczak, Toronto (CA); Graham Burton, Ottawa (CA)

(73) Assignees: Avivagen Inc., Ottawa (CA); National Research Council of Canada, Ottawa (CA)

( * ) Notice: Subject to any disclaimer, the term of this patent is extended or adjusted under 35 U.S.C. 154(b) by 1266 days.

(21) Appl. No.: 12/739,674

(22) PCT Filed: Oct. 23, 2008

(86) PCT No.: PCT/CA2008/001879
§ 371 (c)(1),
(2), (4) Date: Apr. 29, 2011

(87) PCT Pub. No.: WO2009/052629
PCT Pub. Date: Apr. 30, 2009

(65) Prior Publication Data
US 2011/0217244 A1    Sep. 8, 2011

Related U.S. Application Data

(60) Provisional application No. 61/000,583, filed on Oct. 26, 2007.

(51) Int. Cl.
*A61K 31/015* (2006.01)
*A61K 39/39* (2006.01)

(52) U.S. Cl.
CPC .................................. *A61K 39/39* (2013.01)

(58) Field of Classification Search
CPC ... C07C 403/00; C07C 403/14; C07C 403/20; C07C 403/24; A61K 31/12; A61K 31/121; A61K 31/74; A61K 2300/00; A01N 1/00
See application file for complete search history.

(56) References Cited

U.S. PATENT DOCUMENTS

| | | |
|---|---|---|
| 2,988,045 A | 6/1961 | Fisher |
| 3,206,316 A | 9/1965 | Klaui |
| 4,105,855 A | 8/1978 | Schulz et al. |
| 4,127,455 A | 11/1978 | Schulz et al. |
| 4,234,575 A | 11/1980 | Weir et al. |
| 4,333,922 A | 6/1982 | Herschler |
| 4,351,346 A | 9/1982 | Brummer et al. |
| 4,642,318 A | 2/1987 | Wolff |
| 4,702,929 A | 10/1987 | Lehn et al. |
| 4,889,847 A | 12/1989 | Kligman et al. |
| 4,996,069 A | 2/1991 | de Hey et al. |
| 5,047,231 A | 9/1991 | Spanier et al. |
| 5,084,292 A | 1/1992 | Van Dort et al. |
| 5,097,063 A | 3/1992 | Moldt |
| 5,225,604 A | 7/1993 | Moldt |
| 5,252,604 A | 10/1993 | Nagy et al. |
| 5,290,605 A | 3/1994 | Shapira |
| 5,310,554 A | 5/1994 | Haigh |
| 5,358,915 A | 10/1994 | Nebergall et al. |
| 5,475,006 A | 12/1995 | Burton et al. |
| 5,527,533 A | 6/1996 | Tso et al. |
| 5,635,237 A | 6/1997 | Greenberg et al. |
| 5,646,186 A | 7/1997 | Wang et al. |
| 5,665,776 A | 9/1997 | Yu et al. |
| 5,670,548 A | 9/1997 | Bernhard et al. |
| 5,673,653 A | 10/1997 | Sherrill |
| 5,719,195 A | 2/1998 | Braiman |
| 5,744,502 A | 4/1998 | Lignell et al. |
| 5,759,528 A | 6/1998 | Yamada et al. |
| 5,874,093 A | 2/1999 | Eliaz et al. |
| 5,941,197 A | 8/1999 | Axelrod |
| 5,965,616 A | 10/1999 | Wang et al. |
| 5,998,395 A | 12/1999 | Kligman |
| 6,008,254 A | 12/1999 | Kligman et al. |
| 6,080,393 A | 6/2000 | Liu et al. |
| 6,083,520 A | 7/2000 | Toneby |
| 6,093,427 A | 7/2000 | Axelrod |
| 6,110,521 A | 8/2000 | Axelrod |
| 6,159,516 A | 12/2000 | Axelrod et al. |
| 6,207,142 B1 * | 3/2001 | Odds et al. .................. 424/70.8 |
| 6,223,693 B1 | 5/2001 | Perlberg et al. |
| 6,228,887 B1 | 5/2001 | Kligman et al. |
| 6,251,953 B1 | 6/2001 | Baranowitz |
| 6,277,420 B1 | 8/2001 | Andersen et al. |
| 6,296,877 B1 | 10/2001 | Auweter et al. |
| 6,423,743 B1 | 7/2002 | Romancyzk, Jr. |
| 6,433,025 B1 | 8/2002 | Lorenz |

(Continued)

FOREIGN PATENT DOCUMENTS

| AU | 2008316225 A1 | 4/2009 |
|---|---|---|
| CA | 2085212 A1 | 6/1993 |

(Continued)

OTHER PUBLICATIONS

Okajima et al., IOVS, Jul. 2006, 2971-2975.*
Loberto et al., Brazilian Journal of Microbiology (2004) 35:64-68.*
Spellberg et al., Clinical Infectious Diseases, 2008, 46, pp. 155-164.*
U.S. Appl. No. 08/527,039, filed Sep. 12, 1995, Burton et al.
Alaoui-Jamali et al., "In Vivo Reversal of Doxorubicin Resistance by a New Tiapamil Analog Ro11-2933," *J. Pharmacol. Exp. Ther.* 264:1299-1304 (1993).
Alija et al., "Cytotoxic and Genotoxic Effects of Beta-Carotene Breakdown Products on Primary Rat Hepatocytes," *Carcinogenesis* 25:827-831 (2004).
Anonymous, "Vitamin A, Tumor Initiation and Tumor Protection," *Nutr. Rev.* 37:153-156 (1979).

(Continued)

*Primary Examiner* — Shobha Kantamneni
(74) *Attorney, Agent, or Firm* — Clark & Elbing LLP

(57) ABSTRACT

The use of oxidatively transformed carotenoid or a component thereof to enhance the immune response in a subject for the treatment of infection or to enhance the immune response to an antigen in a subject being immunized. Also disclosed are pharmaceutical compositions and kits containing the oxidatively transformed carotenoid.

19 Claims, 9 Drawing Sheets

(56) References Cited

U.S. PATENT DOCUMENTS

| | | |
|---|---|---|
| 6,544,532 B1 | 4/2003 | Jager-Lezer et al. |
| 6,821,538 B2 | 11/2004 | Axelrod et al. |
| 6,840,196 B2 | 1/2005 | Kirch |
| 6,886,496 B1 | 5/2005 | Brown |
| 6,886,497 B1 | 5/2005 | Hague |
| 6,895,900 B2 | 5/2005 | Hingst |
| 7,001,889 B2 | 2/2006 | Freehauf et al. |
| 7,132,458 B2 | 11/2006 | Burton et al. |
| 8,211,461 B2 | 7/2012 | Burton et al. |
| 2002/0088403 A1 | 7/2002 | Heinzl et al. |
| 2002/0165285 A1 | 11/2002 | Runge et al. |
| 2003/0096875 A1 | 5/2003 | Burton et al. |
| 2003/0157159 A1 | 8/2003 | Franklin et al. |
| 2003/0180349 A1 | 9/2003 | Franklin |
| 2003/0190343 A1 | 10/2003 | Thombre et al. |
| 2004/0047896 A1 | 3/2004 | Malnoe et al. |
| 2005/0205086 A1 | 9/2005 | Tamarkin et al. |
| 2005/0249787 A1 | 11/2005 | Reynolds et al. |
| 2006/0063835 A1 | 3/2006 | De Paoli Ambrosi et al. |
| 2006/0127505 A1 | 6/2006 | Haines et al. |
| 2007/0043046 A1 | 2/2007 | Bernardon et al. |
| 2007/0098820 A1 | 5/2007 | Bortlik et al. |
| 2007/0269526 A1 | 11/2007 | Bos et al. |
| 2007/0282010 A1 | 12/2007 | Aberg |
| 2007/0298077 A1 | 12/2007 | Jones |
| 2008/0025929 A1 | 1/2008 | Burton et al. |
| 2008/0107652 A1 | 5/2008 | Durvasula et al. |
| 2008/0107768 A1 | 5/2008 | Hinojosa et al. |
| 2008/0214518 A1 | 9/2008 | Remmal |
| 2008/0311175 A1 | 12/2008 | Burton et al. |
| 2009/0306222 A1 | 12/2009 | Burton et al. |
| 2011/0217244 A1 | 9/2011 | Johnston et al. |
| 2013/0131183 A1 | 5/2013 | Daroszewski et al. |
| 2013/0156816 A1 | 6/2013 | Stobbs et al. |
| 2016/0287528 A1 | 10/2016 | Stobbs et al. |

FOREIGN PATENT DOCUMENTS

| | | |
|---|---|---|
| CA | 2 171 625 | 2/1996 |
| CA | 2 221 122 | 5/1998 |
| CA | 2 357 275 | 10/2002 |
| CA | 2 455 747 | 2/2003 |
| CA | 2 474 208 | 8/2003 |
| CA | 2 495 355 | 2/2004 |
| CA | 2648282 A1 | 10/2007 |
| CA | 2171625 C | 10/2008 |
| CA | 2771204 A1 | 11/2010 |
| CA | 2840376 A1 | 12/2012 |
| CN | 1131939 A | 9/1996 |
| CN | 1253498 A | 5/2000 |
| CN | 1505602 A | 6/2004 |
| EP | 0 385 335 A2 | 9/1990 |
| EP | 0 415 464 A2 | 3/1991 |
| EP | 0546870 A1 | 6/1993 |
| EP | 0 399 619 B1 | 12/1994 |
| EP | 0 630 578 A2 | 12/1994 |
| EP | 0 718 284 A2 | 6/1996 |
| EP | 1 186 245 A2 | 3/2002 |
| EP | 1 253 131 A1 | 10/2002 |
| GB | 1 021 537 | 3/1966 |
| GB | 1 323 800 | 7/1973 |
| GB | 1 502 895 | 3/1978 |
| JP | 06-276956 A | 4/1994 |
| JP | 6-197703 A | 7/1994 |
| JP | 2000103740 A | 4/2000 |
| RU | 2211048 C1 | 8/2003 |
| WO | WO 93/15740 | 8/1993 |
| WO | WO 96/05160 | 2/1996 |
| WO | WO 96/34601 | 11/1996 |
| WO | WO-97/08960 A1 | 3/1997 |
| WO | WO 98/44808 | 10/1998 |
| WO | WO-98/47392 A1 | 10/1998 |
| WO | WO 99/30701 | 6/1999 |
| WO | WO-99/45792 A1 | 9/1999 |
| WO | WO 01/10901 | 2/2001 |
| WO | WO 01/24787 | 4/2001 |
| WO | WO 02/085831 | 10/2002 |
| WO | WO-03/013268 A1 | 2/2003 |
| WO | WO-03/049726 A1 | 6/2003 |
| WO | WO-03/066583 A1 | 8/2003 |
| WO | WO-03/094908 A1 | 11/2003 |
| WO | WO-2004/016099 A1 | 2/2004 |
| WO | WO-2004/016214 A2 | 2/2004 |
| WO | WO-2004/019929 A1 | 3/2004 |
| WO | WO-2004/039171 A1 | 5/2004 |
| WO | WO 2005/079143 | 9/2005 |
| WO | WO-2005/099478 A1 | 10/2005 |
| WO | WO 2006/034570 | 4/2006 |
| WO | WO-2006/120494 A1 | 11/2006 |
| WO | WO 2006/120565 | 11/2006 |
| WO | WO-2006/120567 A2 | 11/2006 |
| WO | WO-2007/007198 A2 | 1/2007 |
| WO | WO-2007/011330 A1 | 1/2007 |
| WO | WO 2007/043046 | 4/2007 |
| WO | WO 2007/112587 | 10/2007 |
| WO | WO 2009/052629 | 4/2009 |
| WO | WO 2010/124391 | 11/2010 |
| WO | WO 2010/124392 | 11/2010 |
| WO | WO-2011/103464 A1 | 8/2011 |

OTHER PUBLICATIONS

Anonymous, "Chemaphor Announces Positive Results of Pilot Canine Clinical Trial of an Oximunol™ Supplement," Medical News Today, Feb. 2, 2010 (available at www.medicalnewstoday.com/articles/177855.php).

Blount et al., "Carotenoid Modulation of Immune Function and Sexual Attractiveness in Zebra Finches," *Science* 300:125-127 (2003).

Brooks et al., "Recent Developments in the Chemistry, Biochemistry, Geochemistry and Post-Tetrad Ontogeny of Sporopollenins Derived from Pollen and Spore Exines," in *Pollen Development and Physiology*, pp. 99-114 (ed. J. Heslop-Harris, Butterworths, London 1971).

Brouwer et al., "A New Synthesis of 4-OR*-3-penten-1-ynes ($C_5$-Fragment) as a Tool for the Preparation of Vitamin A," *J. Royal Netherlands Chem. Soc.* 98:316-320 (1979).

Burton et al., "Beta-Carotene: An Unusual Type of Lipid Antioxidant," *Science* 224:569-573 (1984).

Chew, "Role of Carotenoids in the Immune Response," *J. Dairy Sci.* 76:2804-2811 (1993).

Clark et al., "Retinoic Acid Oxidation at High Oxygen Pressures: Evidence for Spin-Forbidden Direct Addition of Triplet Molecular Oxygen," *J. Am. Chem. Soc.* 119:9560-9561 (1997).

Deming et al., "Mammalian Carotenoid Absorption and Metabolism," *Pure Appl. Chem.* 71:2213-2223 (1999).

El-Tinay et al., "Oxidation of Beta-Carotene. Site of Initial Attack," *J. Org. Chem.* 35:2290-2293 (1970).

Giuliani et al., "Preliminary Observations with an Ointment Containing Tretinoin (Retinoic Acid), Salicylic Acid, Sulfur, Betamethasone, Camphor and Allantoin in Hyperkeratotic Dermatosis," *Chronica Dermatologica* 5:581-594 (1974).

Hill et al., "Retinoids and Cancer Prevention," *Annu. Rev. Nutr.* 12:161-181 (1992).

Hong et al., "Recent Advances in Chemoprevention of Cancer," *Science* 278:1073-1077 (1997).

Hoskinson et al., "Age-Related Changes in Mitogen-Induced Lymphocyte Proliferation and Polymorphonuclear Neutrophil Function in the Piglet," *J. Anim. Sci.* 68:2471-2478 (1990).

Hunter et al., "The Oxidation of Beta-Carotene in Solution by Oxygen," *J. Chem. Soc.* Jan:1-4 (1947).

Kanasawud et al., "Mechanism of Formation of Volatile Compounds by Thermal Degradation of Cartenoids in Aqueous Medium. 2. Lycopene Degradation," *J. Agric. Food Chem.* 38:1238-1242 (1990).

Kiefer et al., "Identification and Characterization of a Mammalian Enzyme Catalyzing the Asymmetric Oxidative Cleavage of Provitamin A," *J. Biol. Chem.* 276:14110-14116 (2001).

(56) References Cited

OTHER PUBLICATIONS

Kim et al., "Dietary Lutein Stimulates Immune Response in the Canine," *Vet. Immunol. Immunopathol.* 74:315-327 (2000).
Krinsky et al., "Actions of Carotenoids in Biological Systems," *Annu. Rev. Nutr.* 13:561-587 (1993).
Lee et al., "Addition of Beta-Ionone to the Diet Fails to Affect Growth Performance in Female Broiler Chickens," *Anim. Feed Sci. Technol.* 106:219-223 (2003).
Martin et al., "Chemistry of Carotenoid Oxidation and Free Radical Reactions," *Pure Appl. Chem.* 71:2253-2262 (1999).
Marty et al., "Degradation of Trans-Beta-Carotene During Heating in Sealed Glass Tubes and Extrusion Cooking," *J. Food. Sci.* 51:698-702 (1986).
Marty et al., "Degradation Products of Trans-Beta-Carotene Produced During Extrusion Cooking," *J. Food. Sci.* 53:1880-1886 (1988).
Mathews-Roth, "Carotenoids and Cancer Prevention: Experimental and Epidemiological Studies," *Pure Appl. Chem.* 57:717-722 (1985).
Mordi et al., "Exploratory Study of Beta-Carotene Autoxidation," *Tetrahedron Lett.* 32:4203-4206 (1991).
Mordi et al., "Oxidative Degradation of Beta-Carotene and Beta-Apo-8'-Carotenal," *Tetrahedron* 49:911-928 (1993).
Morganti et al., "Protective Effects of Oral Antioxidants on Skin and Eye Function," *SKINmed* 3:310-316 (2004).
Onyewu et al., "Characterization of Beta-Carotene Thermal Degradation Products in a Model Food System," *J. Am. Oil Chem. Soc.* 63:1437-1441 (1986).
Oyler et al., "Characterization of Autoxidation Products of Retinoid Acid," *Tetrahedron* 45:7679-7694 (1989).
Peto et al., "Can Dietary Beta-Carotene Materially Reduce Human Cancer Rates?" *Nature* 290:201-208 (1981).
Ramos-Gomez et al., "Sensitivity to Carcinogenesis is Increased and Chemoprotective Efficacy of Enzyme Inducers is Lost in nrf2 Transcription Factor-Deficient Mice," *Proc. Natl. Acad. Sci. USA* 98:3410-3415 (2001).
Russell, "The Enigma of Beta-Carotene in Carcinogenesis: What Can Be Learned from Animal Studies," *J. Nutr.* 134:262S-268S (2004).
Talalay, "Chemoprotection Against Cancer by Induction of Phase 2 Enzymes," *BioFactors* 12:5-11 (2000).
Talalay et al., "Importance of Phase 2 Gene Regulation in Protection Against Electrophile and Reactive Oxygen Toxicity and Carcinogenesis," *Adv. Enzyme Regul.* 43:121-134 (2003).
Trosko et al., "Gap Junctions as Targets for Cancer Chemoprevention and Chemotherapy," *Curr. Drug Targets* 3:465-482 (2002). (pp. 1-17).
Verma et al., "Inhibition of Skin Tumor Promotion by Retinoic Acid and Its Metabolite 5,6-Epoxyretinoic Acid," *Cancer Res.* 40:2367-2371 (1980).
Wang, "Can Smoke-Exposed Ferrets be Utilized to Unravel the Mechanisms of Action of Lycopene?" *J. Nutr.* 135:2053S-2056S (2005).
International Search Report for PCT/CA2008/001879 (dated Feb. 2, 2009).
International Preliminary Report on Patentability for PCT/CA2008/001879 (dated Apr. 27, 2010).
Communication from the European Patent Office for EP 05736675 (dated Feb. 2, 2010).
Communication from the European Patent Office for European Patent Application No. 08842588.9, dated Feb. 19, 2013 (6 pages).
Extended European Search Report for European Application No. 08842588.9, dated Jun. 28, 2012 (10 pages).
First Examination Report for Indian Application No. 3064/CHENP/2010, dated Jul. 30, 2014 (3 pages).
Office Action for Chinese Application No. 200880122743.9, dated Jul. 20, 2011 (17 pages).
Office Action for Japanese Application No. 2010-530236, dated Jun. 18, 2013 (8 pages).
Office Action for Japanese Application No. 2010-530236, dated Sep. 2, 2014 (7 pages).

Armand et al., "Specificity of the phase I trial for cytotoxic drugs in oncology," Fundam Clin Pharmacol. 4 Suppl 2:197s-204s (1990).
Brown et al., "New anticancer agents," Cancer Chemother Biol Response Modif. 13:115-55 (1992).
Communication from the European Patent Office for European Application No. 10769196.6, dated May 31, 2013 (5 pages).
Database Biosis for PREV200300291110, "Addition of beta-ionone to the diet fails to affect growth performance in female broiler chickens," (2003) (1 page).
English translation of Unfavorable Patentability Opinion for Brazilian Application No. PI 0516202-5, received Jan. 20, 2015 (4 pages).
Examination Report for Australian Patent Application No. 2010242502, dated Jan. 21, 2015 (5 pages).
Extended European Search Report and Search Opinion for European Application No. 10769196.6, dated Sep. 27, 2013 (6 pages).
Extended European Search Report for European Application No. 05791352.7, dated Feb. 14, 2008 (5 pages).
Extended European Search Report for European Patent Application No. 11745354.8, dated May 2, 2014 (8 pages).
FAO, "Fish feeds and feeding," <ftp://ftp.fao.org/fi/cdrom/fao_training/FAO_Training/General/x6709e/x6709e10.htm>, retrieved on Mar. 19, 2015 (45 pages).
Hardman et al., Principles of therapeautics. *Goodman & Gilman's the Pharmacological Basis of Therapeutics*. 9th Edition. 51, 57-8 (1996).
Hawkins et al., "New anticancer agents: taxol, camptothecin analogs, and anthrapyrazoles," Oncology. 6(12):17-23 (1992).
International Preliminary Report on Patentability and Written Opinion for International Application No. PCT/CA2010/000671, dated Nov. 1, 2011 (10 pages).
International Preliminary Report on Patentability and Written Opinion in International Patent Application No. PCT/US2011/025481, dated Aug. 21, 2012 (13 pages).
International Preliminary Report on Patentability for International Application No. PCT/CA2005/001458, dated Feb. 7, 2007 (6 pages).
International Search Report and Written Opinion for International Application No. PCT/CA2010/000671, dated Jul. 14, 2010 (14 pages).
International Search Report for International Application No. PCT/CA2005/001458, dated Jan. 3, 2006 (3 pages).
International Search Report for International Application No. PCT/CA2008/001879, dated Feb. 2, 2009 (6 pages).
Iwan'ska et al., "Carotenoids content of green forages and preserved feeds," Acta Acad Agri Ac Tech Olstenesis Zootechnica. 47:117-28 (1997) retrieved from CABI Abstracts. (Abstract only) (2 pages).
Magnadóttir, "Innate immunity of fish (overview)," Fish Shellfish Immunol. 20(2):137-51 (2006).
Office Action for Chilean Patent Application No. 2012-002309, dated Aug. 6, 2014 (19 pages).
Office Action for Chilean Patent Application No. 2012-002309, dated Apr. 20, 2015 (23 pages).
Rudnic et al., Oral Solid Dosage Forms. *Remington: The Science and Practice of Pharmacy*. Gennaro, 858-61 (2000).
Sciarra et al., Aerosols. *Remington: The Science and Practice of Pharmacy*. Gennaro, 963 (2000).
Supplementary European Search Report for European Application No. 05736675.9, dated Sep. 18, 2009 (3 pages).
Tacon, "The nutrition and feeding of farmed fish and shrimp. A training manual: Feeding methods—complete diet feeding," FAO Corporate Document Repository Jun. 1987, <http://www.fao.org/docrep/field/003/ab467e/ab467e.htm> retrieved on Aug. 30, 2014 (27 pages).
Webster's New Collegiate Dictionary. Merriam-Webster (ed.), 49 (1977).
Weiss et al., "New anticancer agents," Cancer Chemother Biol Reponse Modif. 14:118-28 (1993).
Wikipedia, "Polysorbate 80," <http://en.wikipedia.org/wiki/Polysorbate_80>, retrieved on Nov. 20, 2013 (4 pages).
Johnson, et al., "Treatment of Seborrheic Dermatitis," American Family Physician, <http://www.aafp.org/afp/2000/0501/p2703.html>, retrieved Jun. 18, 2015 (6 pages).

(56) References Cited

OTHER PUBLICATIONS

Shojadoost et al., "The successful experimental induction of necrotic enteritis in chickens by Clostridium perfringens: a critical review," Vet Res. 43:74 (2012) (12 pages).

Office Action for Canadian Patent Application No. 2,771,204, dated Apr. 8, 2016 (5 pages).

Johnston et al., "Biologically active polymers from spontaneous carotenoid oxidation: a new frontier in carotenoid activity," PLoS One. 9(10):e111346 (2014) (10 pages).

Burton et al., "beta-Carotene autoxidation: oxygen copolymerization, non-vitamin A products, and immunological activity," Can J Chem. 92(4):305-16 (2014).

Burton et al., "Discovery and characterization of carotenoid-oxygen copolymers in fruits and vegetables with potential health benefits," J Agric Food Chem. 64(19):3767-77 (2016).

Duquette et al., "Anti-inflammatory effects of retinoids and carotenoid derivatives on caspase-3-dependent apoptosis and efferocytosis of bovine neutrophils," Am J Vet Res. 75(12):1064-75 (2014).

Oro et al., "Splitting hairs: dissecting roles of signaling systems in epidermal development," Cell 95(5):575-8 (1998).

Waldenstedt et al., "Effects of astaxanthin-rich algal meal (Haematococcus pluvalis) on growth performance, caecal campylobacter and clostridial counts and tissue astaxanthin concentration of broiler chickens," Animal Feed Science and Technology 108:119-32 (2003).

\* cited by examiner

COMPOSITIONS AND METHODS FOR ENHANCING IMMUNE RESPONSE

CROSS-REFERENCE TO RELATED APPLICATIONS

This application is the U.S. National Stage of International Application PCT/CA2008/001879, filed on Oct. 23, 2008, which claims the benefit of U.S. Provisional Application Ser. No. 61/000,583, filed Oct. 26, 2007.

BACKGROUND OF THE INVENTION

The invention relates to the use of carotenoid oxidation products for enhancing immune response.

Multicellular organisms have developed two general systems of immunity to infectious agents. The two systems are innate or natural immunity (also known as "innate immunity") and adaptive (acquired) or specific immunity. The major difference between the two systems is the mechanism by which they recognize infectious agents.

The innate immune system uses a set of germline-encoded receptors for the recognition of conserved molecular patterns present in microorganisms. These molecular patterns occur in certain constituents of microorganisms including: lipopolysaccharides, peptidoglycans, lipoteichoic acids, phosphatidyl cholines, bacteria-specific proteins, including lipoproteins, bacterial DNAs, viral single and double-stranded RNAs, unmethylated CpG-DNAs, mannans and a variety of other bacterial and fungal cell wall components. Such molecular patterns can also occur in other molecules such as plant alkaloids. These targets of innate immune recognition are called Pathogen Associated Molecular Patterns (PAMPs) since they are produced by microorganisms and not by the infected host organism. The receptors of the innate immune system that recognize PAMPs are called Pattern Recognition Receptors (PRRs) (see Janeway et al., *Cold Spring Harb. Symp. Quant. Biol.* 54:1 (1989); Medzhitov et al., *Curr. Opin. Immunol.* 94:4 (1997)). These receptors vary in structure and belong to several different protein families. Some of these receptors recognize PAMPs directly (e.g., CD14, DEC205, collectins), while others (e.g., complement receptors) recognize the products generated by PAMP recognition. Members of these receptor families can, generally, be divided into three types: (1) humoral receptors circulating in the plasma; (2) endocytic receptors expressed on immune-cell surfaces, and (3) signaling receptors that can be expressed either on the cell surface or intracellularly. (Medzhitov et al., *Curr. Opin. Immunol.* 94:4 (1997); Fearon et al., *Science* 272:50 (1996)).

Cellular PRRs are expressed on effector cells of the innate immune system, including cells that function as professional antigen-presenting cells (APC) in adaptive immunity, such as macrophages, dendritic cells, B lymphocytes and surface epithelia. This expression profile allows PRRs to directly induce innate effector mechanisms, and also to alert the host organism to the presence of infectious agents by inducing the expression of a set of endogenous signals, such as inflammatory cytokines and chemokines, as discussed below. This latter function allows efficient mobilization of effector forces to combat the invaders.

In contrast, the adaptive immune system, which is found only in vertebrates, uses two types of antigen receptors that are generated by somatic mechanisms during the development of each individual organism. The two types of antigen receptors are the T-cell receptor (TCR) and the immunoglobulin receptor (IgR), which are expressed on two specialized cell types, T-lymphocytes and B-lymphocytes, respectively. The specificities of these antigen receptors are generated at random during the maturation of lymphocytes by the processes of somatic gene rearrangement, random pairing of receptor subunits, and by a template-independent addition of nucleotides to the coding regions during the rearrangement.

The innate immune system plays a crucial role in the control of initiation of the adaptive immune response and in the induction of appropriate cell effector responses (Fearon et al., *Science* 272:50 (1996)). It is now well established that the activation of naive T-lymphocytes requires two distinct signals: one is a specific antigenic peptide recognized by the TCR, and the other is the so called co-stimulatory signal, B7, which is expressed on APCs and recognized by the CD28 molecule expressed on T-cells (Lenschow et al., *Annu. Rev. Immunol.* 14:233 (1996)). Activation of naive $CD4^+$ T-lymphocytes requires that both signals, the specific antigen and the B7 molecule, are expressed on the same APC. If a naive CD4 T-cell recognizes the antigen in the absence of the B7 signal, the T-cell will die by apoptosis. Expression of B7 molecules on APCs, therefore, controls whether or not the naive CD4 T-lymphocytes will be activated. Since CD4 T-cells control the activation of CD8 T-cells for cytotoxic functions, and the activation of B-cells for antibody production, the expression of B7 molecules determines whether or not an adaptive immune response will be activated.

The innate immune system plays a crucial role in the control of B7 expression (Fearon et al., *Science* 272:50 (1996); Medzhitov et al., *Cell* 91:295 (1997)). As mentioned earlier, innate immune recognition is mediated by PRRs that recognize PAMPs. Recognition of PAMPs by PRRs results in the activation of signaling pathways that control the expression of a variety of inducible immune response genes, including the genes that encode signals necessary for the activation of lymphocytes, such as B7, cytokines and chemokines (Medzhitov et al., *Cell* 91:295 (1997); Medzhitov et al., *Nature* 388:394 (1997)). Induction of B7 expression by PRR upon recognition of PAMPs thus accounts for self/nonself discrimination and ensures that only T-cells specific for microorganism-derived antigens are normally activated. This mechanism normally prevents activation of autoreactive lymphocytes specific for self-antigens.

Receptors of the innate immune system that control the expression of B7 molecules and cytokines have recently been identified. (Medzhitov et al., *Nature* 388:394 (1997); Rock et al., *Proc. Natl. Acad. Sci. USA,* 95:588 (1998)). These receptors belong to the family of Toll-like receptors (TLRs), so called because they are homologous to the *Drosophila* Toll protein which is involved both in dorsoventral patterning in *Drosophila* embryos and in the immune response in adult flies (Lemaitre et al., *Cell* 86:973 (1996)). In mammalian organisms, such TLRs have been shown to recognize PAMPs such as the bacterial products LPS, peptidoglycan, and lipoprotein (Schwandner et al., *J. Biol. Chem.* 274:17406 (1999); Yoshimura et al., *J. Immunol.* 163:1 (1999); Aliprantis et al., *Science* 285:736 (1999)).

Vaccines have traditionally been used as a means to protect against disease caused by infectious agents, and with the advancement of vaccine technology, vaccines have been used in additional applications that include, but are not limited to, control of mammalian fertility, modulation of hormone action, and prevention or treatment of tumors. The primary purpose of vaccines used to protect against a disease is to induce immunological memory to a particular microorganism. More generally, vaccines are needed to induce an immune response to specific antigens, whether they belong to a microorganism or are expressed by tumor cells or other diseased or abnormal cells. Division and differentiation of B- and T-lymphocytes that have surface receptors specific for the antigen generate both specificity and memory.

In order for a vaccine to induce a protective immune response, it must fulfill the following requirements: 1) it must include the specific antigen(s) or fragment(s) thereof that will be the target of protective immunity following vaccination; 2) it must present such antigens in a form that can be recognized by the immune system, e.g., a form resistant to degradation prior to immune recognition; and 3) it must activate APCs to present the antigen to $CD4^+$ T-cells, which in turn induce B-cell differentiation and other immune effector functions.

Conventional vaccines contain suspensions of attenuated or killed microorganisms, such as viruses or bacteria, incapable of inducing severe infection by themselves, but capable of counteracting the unmodified (or virulent) species when inoculated into a host. Usage of the term has now been extended to include essentially any preparation intended for active immunologic prophylaxis (e.g., preparations of killed microbes of virulent strains or living microbes of attenuated (variant or mutant) strains; microbial, fungal, plant, protozoan, or metazoan derivatives or products; and synthetic vaccines). Examples of vaccines include, but are not limited to, cowpox virus for inoculating against smallpox, tetanus toxoid to prevent tetanus, whole-inactivated bacteria to prevent whooping cough (pertussis), polysaccharide subunits to prevent streptococcal pneumonia, and recombinant proteins to prevent hepatitis B.

Although attenuated vaccines are usually immunogenic, their use has been limited because their efficacy generally requires specific, detailed knowledge of the molecular determinants of virulence. Moreover, the use of attenuated pathogens in vaccines is associated with a variety of risk factors that in most cases prevent their safe use in humans.

The problem with synthetic vaccines, on the other hand, is that they are often non-immunogenic or non-protective. The use of available adjuvants to increase the immunogenicity of synthetic vaccines is often not an option because of unacceptable side effects induced by the adjuvants themselves.

An adjuvant is any substance that increases the immunogenicity of an antigen. Although chemicals such as alum are often considered to be adjuvants, they are in effect akin to carriers and are likely to act by stabilizing antigens and/or promoting their interaction with antigen-presenting cells. The best adjuvants are those that mimic the ability of microorganisms to activate the innate immune system. Pure antigens do not induce an immune response because they fail to induce the costimulatory signal (e.g., B7.1 or B7.2) necessary for activation of lymphocytes. Thus, a key mechanism of adjuvant activity has been attributed to the induction of costimulatory signals by microbial, or microbial-like, constituents carrying PAMPs that are routine constituents of adjuvants (see Janeway et al., *Cold Spring Harb. Symp. Quant. Biol.* 54: 1 (1989)). As discussed above, the recognition of these PAMPs by PRRs induces the signals necessary for lymphocyte activation (such as B7) and differentiation (effector cytokines).

The benefit of incorporating adjuvants into vaccine formulations to enhance immunogenicity must be weighed against the risk that these agents will induce adverse local and/or systemic reactions. Local adverse reactions include local inflammation at the injection site and, rarely, the induction of granuloma or sterile abscess formation. Systemic reactions to adjuvants observed in laboratory animals include malaise, fever, adjuvant arthritis, and anterior uveitis (Allison et al., *Mol. Immunol.* 28:279 (1991); Waters et al., *Infect. Immun.,* 51:816 (1986)). Such reactions often may be due to the cytokine profile the adjuvant induces. Thus, many potent adjuvants, such as Freund's Complete or Freund's Incomplete Adjuvant, are toxic and are therefore useful only for animal research purposes, not human vaccinations.

Alum is currently approved for use as a clinical adjuvant, even though it has relatively limited efficacy, because it is not an innate immune stimulant and thus does not cause excessive inflammation.

There is therefore a need for adjuvants which increase the immunogenicity of antigens without producing a proinflammatory response. There is also a need for immune system modulators capable of sensitizing, or priming, the innate and adaptive immune system to produce a more rapid and effective response to an infection by the host, or to enhance the efficacy of antibiotics.

SUMMARY OF THE INVENTION

The invention provides compositions, methods, and kits for the administration of oxidatively transformed carotenoid and components thereof. The compositions can be useful for sensitizing the innate and adaptive immune system of a subject and thus can be used to treat an infection or as an adjuvant in an immunization.

In a first aspect, the invention features a method of treating a subject having an infection by administering to the subject oxidatively transformed carotenoid, or a component thereof, in an amount sufficient to treat the infection.

In a related aspect, the invention features a method of treating a human subject having, or at risk of, an infection by administering to the subject oxidatively transformed carotenoid, or a component thereof, in an amount sufficient to treat the infection.

In another related aspect, the invention features a method of treating a subject having, or at risk of, an infection by administering to the subject oxidatively transformed carotenoid in an amount sufficient to treat the infection, or a component thereof, wherein the oxidatively transformed carotenoid, or a component thereof, is administered intravenously, ocularly, intramuscularly, topically, subcutaneously, or intranasally.

The invention features a method of enhancing immune response in a subject having an infection by administering to the subject an effective amount of oxidatively transformed carotenoid, or a component thereof.

The invention also features a method of enhancing immune response in a human subject having, or at risk of, an infection by administering to the subject an effective amount of oxidatively transformed carotenoid, or a component thereof.

The invention further features a method of enhancing immune response in a human subject having, or at risk of, an infection by administering to the subject an effective amount of oxidatively transformed carotenoid, or a component thereof, wherein the oxidatively transformed carotenoid, or a component thereof, is administered intravenously, ocularly, intramuscularly, topically, subcutaneously, or intranasally.

In certain embodiments of the above methods, the infection is by a bacterium, virus, fungus, or parasite. For example, the infection can be community-acquired pneumonia, upper and lower respiratory tract infection, skin and soft tissue infection, acute bacterial otitis media, bacterial pneumonia, complicated infection, pyelonephritis, intra-abdominal infection, bacterial sepsis, central nervous system infection, bacteremia, wound infection, peritonitis, meningitis, infections after burn, urogenital tract infection, pelvic inflammatory disease, endocarditis, or intravascular infection. The oxidatively transformed carotenoid, or a component thereof, can be administered ocularly for the treatment of an eye infection. In another embodiment, the oxidatively transformed carotenoid, or a component thereof, is administered topically to the mouth of the subject for the treatment of an oral infection.

In still other embodiments of the above methods, the subject has not been diagnosed with, but is at risk of, an infection. Alternatively, the methods are used to treat a subject having an infection.

In certain embodiments of any of the above aspects, the method further includes administering to the subject an antibiotic, wherein the oxidatively transformed carotenoid, or a component thereof, and the antibiotic are administered simultaneously, or within 14 days, 10 days, 7 days, or 3 days of each other.

In a related aspect, the invention features a method of enhancing the adaptive immune response to an antigen in a subject being immunized, the method including (i) administering to the subject an effective amount of oxidatively transformed carotenoid, or a component thereof, and (ii) administering to the subject an antigen, wherein the oxidatively transformed carotenoid, or a component thereof, is administered prior to the antigen.

The invention also features a method of enhancing the adaptive immune response to an antigen in a human subject being immunized, the method including administering to the subject an effective amount of oxidatively transformed carotenoid, or a component thereof.

The invention further features a method of enhancing the adaptive immune response to an antigen in a subject being immunized, the method including administering to the subject an effective amount of oxidatively transformed carotenoid, or a component thereof, wherein the oxidatively transformed carotenoid, or a component thereof, is administered intravenously, ocularly, intramuscularly, topically, subcutaneously, or intranasally.

In a related aspect, the invention features a kit for enhancing adaptive immune response to an antigen in a subject being immunized, including: (i) a pharmaceutical composition including oxidatively transformed carotenoid or a component thereof; (ii) a pharmaceutical composition including an antigen; and (iii) instructions for administering the oxidatively transformed carotenoid or a component thereof, and the antigen for the immunization of a subject.

In any of the above methods or kits directed to enhancing adaptive immune response, the antigen can be derived, for example, from a pathogen, such as a bacterium, virus, fungus, or parasite. In certain embodiments, the antigen is a carbohydrate, glycolipid, glycoprotein, lipid, protein, lipoprotein, phospholipid, or polypeptide. The pathogen can be, for example, a live or an attenuated live virus. In some embodiments, the pathogen is anthrax, influenza, polio, measles, rabies, or any pathogen described herein.

In any of the above methods or kits directed to enhancing adaptive immune response, the oxidatively transformed carotenoid, or a component thereof, can be administered within 14 days, 10 days, 8 days, 6 days, 4 days, 3 days, 2 days, or even 1 day of administering the antigen. In certain embodiments, the antigen is administered prior to the oxidatively transformed carotenoid, or a component thereof. In other embodiments, the oxidatively transformed carotenoid, or a component thereof, is administered prior to the antigen.

In still another embodiment, the oxidatively transformed carotenoid, or a component thereof, is administered simultaneously with the antigen.

In a related aspect, the invention features a pharmaceutical composition including oxidatively transformed carotenoid, or a component thereof, and an antigen. The pharmaceutical composition can be formulated, for example, for oral, intravenous, intramuscular, ophthalmic, topical, subcutaneous, or intranasal administration. In certain embodiments, the antigen can be derived, for example, from a pathogen, such as a bacterium, virus, fungus, or parasite. In certain embodiments, the antigen is a carbohydrate, glycolipid, glycoprotein, lipid, protein, lipoprotein, phospholipid, or polypeptide. The pathogen can be, for example, a live or an attenuated live virus. In some embodiments, the pathogen is anthrax, influenza, polio, measles, rabies, or any pathogen described herein.

In another aspect, the invention features a kit, including: (i) a pharmaceutical composition including oxidatively transformed carotenoid or a component thereof; and (ii) instructions for administering the composition for the treatment of a subject having, or at risk of, an infection. In certain embodiments, the infection is by a bacterium, virus, fungus, or parasite. For example, the infection can be community-acquired pneumonia, upper and lower respiratory tract infection, skin and soft tissue infection, acute bacterial otitis media, bacterial pneumonia, complicated infection, pyelonephritis, intra-abdominal infection, bacterial sepsis, central nervous system infection, bacteremia, wound infection, peritonitis, meningitis, infections after burn, urogenital tract infection, pelvic inflammatory disease, endocarditis, or intravascular infection. In other embodiments, the kit further included instructions for administering an antibiotic to the subject.

The invention also features a toothpaste including oxidatively transformed carotenoid or a component thereof. The toothpaste can be formulated with any excipients known to be useful in making toothpaste, such as those described herein.

The invention further features a mouthwash including oxidatively transformed carotenoid or a component thereof. The mouthwash can be formulated with any excipients known to be useful in making mouthwash, such as those described herein.

The invention also features a pharmaceutical composition including oxidatively transformed carotenoid, or a component thereof, and formulated for administration to an eye. The pharmaceutical composition can be, for example, an ophthalmic drop, ophthalmic salve, opthalmic ointment, ophthalmic spray, subconjunctival injection, or intravitreal injection, contact lens, conjunctival insert, or ocular insert. The pharmaceutical composition can be formulated with any excipients known to be useful in making formulations for delivery to an eye, such as those described herein.

In any of the above methods, compositions, and kits the oxidatively transformed carotenoid, or a component thereof, can include the polymeric component of oxidatively transformed carotenoid. In other embodiments, the oxidatively transformed carotenoid, or a component thereof, includes a component of oxidatively transformed carotenoid that includes 2-methyl-6-oxo-2,4-heptadienal, dihydroactinidiolide, β-cyclocitral, β-ionone, β-ionone 5,6-epoxide, 4-oxo-β-ionone, β-ionylidene acetaldehyde, β-ionylidene acetaldehyde 5,6-epoxide, 4-oxo-β-ionylidene acetaldehyde, β-apo-13-carotenone, β-apo-13-carotenone 5,6-epoxide, 4-oxo-β-apo-13-carotenone, retinal, retinal 5,6-epoxide, or mixtures thereof. In still other embodiments, the oxidatively transformed carotenoid, or a component thereof, includes 2-methyl-6-oxo-2,4-heptadienal. Desirably, the oxidatively transformed carotenoid, or a component thereof, is oxidatively transformed carotenoid. In certain embodiments, the oxidatively transformed carotenoid is an oxidation product of n-carotene, lycopene, retinoic acid, or canthaxanthin.

In any of the above methods, compositions, and kits the oxidatively transformed carotenoid, or a component thereof, can be administered orally, intravenously, intramuscularly, ocularly, topically, subcutaneously, intranasally, or by any other route of administration described herein.

In any of the above methods, compositions, and kits the, the subject can be a human, a domesticated pet (e.g., a dog, cat, horse, or bird), or an agricultural animal, including, for example, sheep, swine, cattle (e.g., dairy cattle or beef cattle), poultry (e.g., turkey or chicken), or fish (e.g., tilapia, catfish, trout, or salmon).

As used herein, an "amount effective" refers to an amount of oxidatively transformed carotenoid, or a component thereof, which sensitizes the innate or adaptive immune system of a subject, thus enhancing immune response to an infection.

By an "amount sufficient" is meant the amount of oxidatively transformed carotenoid, or a component thereof, required to treat or prevent an infection or a disease associated with an infection. The effective amount of a pharmaceutical composition of the invention used to practice the invention for therapeutic or prophylactic treatment of conditions caused by or contributed to by an infection varies depending upon the manner of administration, the age, body weight, and general health of the subject. Ultimately, the attending physician or veterinarian will decide the appropriate amount and dosage regimen. Such amount is referred to as an "amount sufficient."

As used herein, "carotenoid" refers to naturally-occurring pigments of the terpenoid group that can be found in plants, algae, bacteria, and certain animals, such as birds and shellfish. Carotenoids include carotenes, which are hydrocarbons (i.e., without oxygen), and their oxygenated derivatives (i.e., xanthophylls). Examples of carotenoids include lycopene; β-carotene; zeaxanthin; echinenone; isozeaxanthin; astaxanthin; canthaxanthin; lutein; citranaxanthin; β-apo-8'-carotenic acid ethyl ester; hydroxy carotenoids, such as alloxanthin, apocarotenol, astacene, astaxanthin, capsanthin, capsorubin, carotenediols, carotenetriols, carotenols, cryptoxanthin, decaprenoxanthin, epilutein, fucoxanthin, hydroxycarotenones, hydroxyechinenones, hydroxylycopene, lutein, lycoxanthin, neurosporine, phytoene, phytofluoene, rhodopin, spheroidene, torulene, violaxanthin, and zeaxanthin; and carboxylic carotenoids, such as apocarotenoic acid, β-apo-8'-carotenoic acid, azafrin, bixin, carboxylcarotenes, crocetin, diapocarotenoic acid, neurosporaxanthin, norbixin, and lycopenoic acid.

As used herein "component" refers to an active oxidized component of an oxidatively transformed carotenoid mixture that includes either polymeric material or a compound selected from 2-methyl-6-oxo-2,4-heptadienal, dihydroactinidiolide, cyclocitral, β-ionone, β-ionone 5,6-epoxide, 4-oxo-β-ionone, β-ionylidene acetaldehyde, β-ionylidene acetaldehyde 5,6-epoxide, 4-oxo-β-ionylidene acetaldehyde, β-apo-13-carotenone, β-apo-13-carotenone 5,6-epoxide, 4-oxo-β-apo-13-carotenone, retinal, and retinal 5,6-epoxide; and mixtures thereof. Components of oxidatively transformed carotenoid are active in that they are capable of treating infection or enhancing immune response in an animal. Methods for assessing whether a particular fraction of oxidatively transformed carotenoid is capable of treating infection and/or enhancing immune response are provided in the Examples. Methods of fractionating oxidatively transformed carotenoid mixtures into components are described in U.S. Pat. No. 5,475,006 and U.S. Ser. No. 08/527,039, each of which are incorporated herein by reference.

As used herein, "enhancing immune response" refers to an increase in the expression of CD14 or increase phagocytic activity in THP-1 cells in a subject being treated with oxidatively transformed carotenoid, or a component thereof, as described herein in comparison to the same subject prior to being treated.

By "infection" is meant the invasion of a host by microbes (e.g., by bacteria, fungi, or viruses). For example, the infection may include the excessive growth of microbes that are normally present in or on the body of a mammal or growth of microbes that are not normally present in or on a mammal. More generally, an infection can be any situation in which the presence of a microbial population is damaging to a host body. In some instances, microbial growth may be modest, but the damage is caused by production of various toxic constituents by the microbe. In rare cases, microbes grow outside of the host, produce toxins that are ingested and the damage is entirely the result of the activity of this microbial toxin. Thus, a subject is "suffering" from an infection when an excessive amount of a microbial population is present in or on the subject's body, or when the presence of a microbial population is damaging the cells or other tissue of the subject.

As used herein "oxidatively transformed carotenoid" refers to a carotenoid which has been reacted with up to 6 to 8 molar equivalents of oxygen, or an equivalent amount of oxygen from another oxidizing agent, resulting in a mixture of very low molecular weight oxidative cleavage products and a large proportion of polymeric material (i.e., that component of the oxidatively transformed carotenoid having a molecular weight of greater than 1,000 Daltons). The resulting reaction produces a mixture that includes molecular species having molecular weights ranging from about 100 to 8,000 Daltons. The polymeric material is believed to be formed by the many possible chemical recombinations of the various oxidative fragments that are formed. Methods of making oxidatively transformed carotenoid are described in U.S. Pat. No. 5,475,006 and U.S. Ser. No. 08/527,039, each of which are incorporated herein by reference. As used herein, the term "OxBC" refers specifically to oxidatively transformed carotenoid derived from β-carotene.

By "pharmaceutical composition" is meant a composition containing oxidatively transformed carotenoid, or a component thereof, and formulated with one or more pharmaceutical-grade excipients in a manner that conforms with the requirements of a governmental agency regulating the manufacture and sale of pharmaceuticals as part of a therapeutic regimen for the treatment or prevention of disease in a mammal (e.g., manufactured according to GMP regulations and suitable for administration to a human). Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or any other formulation described herein.

By "subject" is meant any vertebrate animal including, without limitation, humans, dogs, cats, horses, sheep, swine, cattle, poultry, and fish.

As used herein, the term "treating" refers to administering a pharmaceutical composition for prophylactic and/or therapeutic purposes. To "prevent disease" refers to prophylactic treatment of a subject who is not yet ill, but who is susceptible to, or otherwise at risk of, a particular disease. To "treat disease" or use for "therapeutic treatment" refers to administering treatment to a subject already suffering from a disease to improve or stabilize the subject's condition. Thus, in the claims and embodiments, treating is the administration to a subject either for therapeutic or prophylactic purposes. As used herein, "at risk of" refers to subjects prone to infections. Subjects can be prone to infections, for example, by virtue of (i) having a weakened immune system (i.e., immuno-compromised subjects) or (ii) exposure to microbes (i.e., as a result of a surgical procedure, regular contact with the public, such as with a school teacher or health worker, or by exposure to an diseased/infectious environment).

The synthesis and purification of 2-methyl-6-oxo-2,4-heptadienal has been reported in U.S. Ser. No. 08/527,039. A more convenient five-step synthetic scheme for the preparation of 2-methyl-6-oxo-2,4-heptadienal is provided in U.S. Ser. No. 10/196,695, published May 22, 2003.

The compositions and methods of the invention can be used to sensitize the innate and adaptive immune systems of a subject to infection.

Other features and advantages of the invention will be apparent from the following Detailed Description, the Drawings, and the Claims.

DETAILED DESCRIPTION

Figure 1:
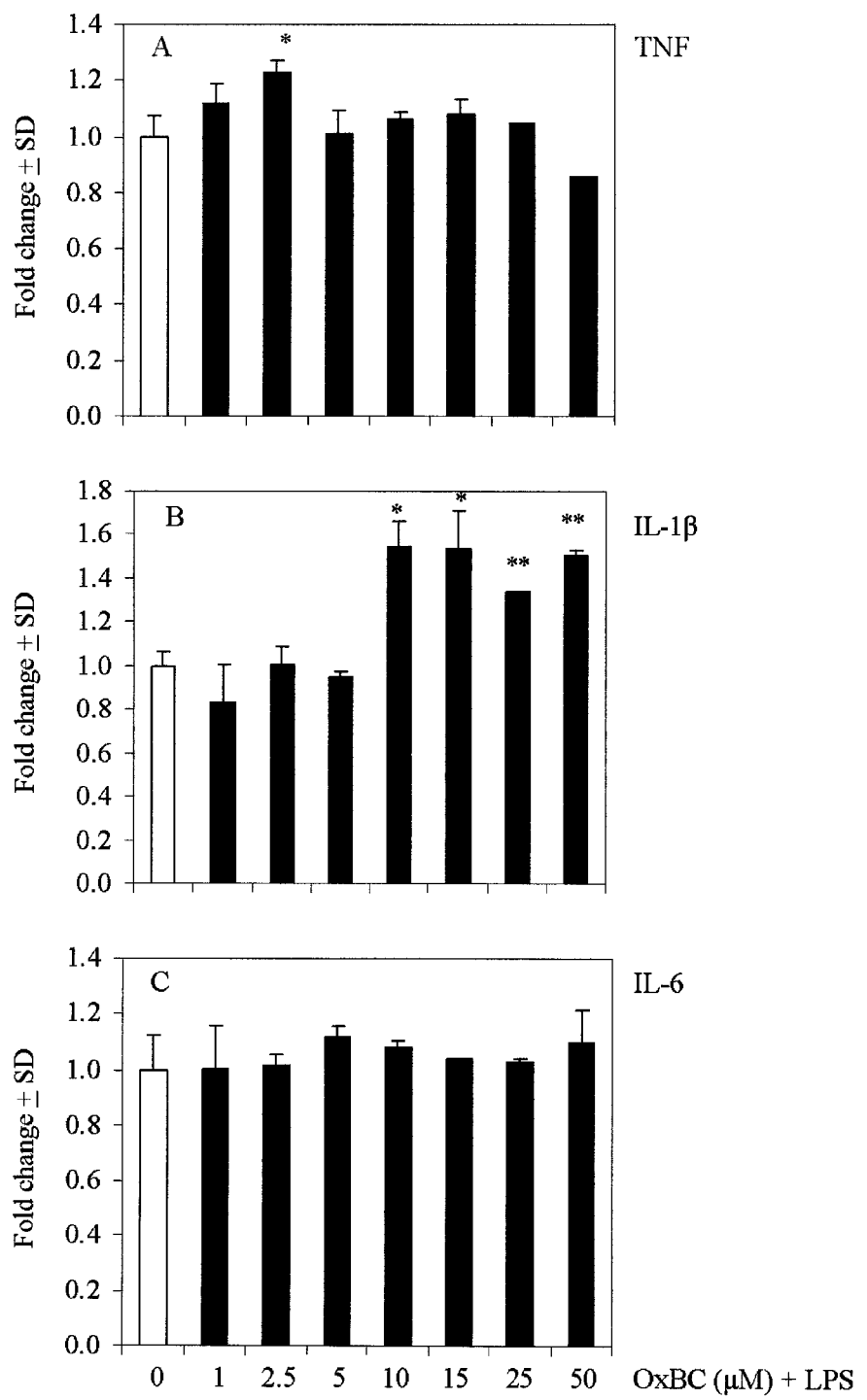
FIG. 1 is a graph depicting TNF (A), IL-1β (B) and IL-6 (C) levels in primary peripheral blood monocytes (PBM) incubated with LPS prior to being treated with OxBC. Primary PBM were incubated with LPS (15 ng/ml) for 24 h prior to being treated with the indicated concentrations of OxBC. After 24 h, CM was harvested and TNF (A), IL-1β (B) and IL-6 (C) levels detected by ELISA (* $p<0.05$, ** $p<0.02$, Students t-test). Purified human monocytes exposed to LPS respond to treatment with OxBC by increased expression of inflammatory cytokine IL-1β suggesting the ability of OxBC to enhance response to microbial infection.

The invention provides compositions, methods, and kits for the administration of oxidatively transformed carotenoid and components thereof. The compositions can be useful for sensitizing the innate and adaptive immune system of a subject to an infection.

Therapy

The invention features methods for sensitizing the innate and adaptive immune system of a subject to an infection.

Therapy according to the invention may be performed alone or in conjunction with another therapy (i.e., in combination with an antibiotic therapy) and may be provided at home, the doctor's office, a clinic, a hospital's outpatient department, or a hospital. The duration of the therapy depends on the type of disease or disorder being treated, the age and condition of the patient, the stage and type of the patient's disease, and how the patient responds to the treatment.

Treating Microbial Infections

The methods and compositions of the invention can be used to treat, for example, respiratory tract infections, acute bacterial otitis media, bacterial pneumonia, urinary tract infections, complicated infections, pyelonephritis, intra-abdominal infections, bacterial sepsis, skin and skin structure infections, soft tissue infections, central nervous system infections, bacteremia, wound infections, peritonitis, meningitis, infections after burn, urogenital tract infections, pelvic inflammatory disease, endocarditis, intravascular infections, and any other infections described herein.

Increasing the Immunogenicity of Antigens

The methods and compositions of the invention can be used to increase the immunogenicity of antigens (i.e., as an adjuvant used in immunizations). Diseases against which the subject may be immunized include all diseases capable of being treated or prevented by immunization, such as viral diseases, allergic manifestations, diseases caused by bacterial or other pathogens which enter through or colonise mucosal surfaces, AIDS, autoimmune diseases such as systemic Lupus Erythe-matosus, and cancers. Examples of viral infections which may be treated or prevented using the invention include infection by DNA viruses, such as EBV and VZV, and in particular herpesviridae, for example HSV and HCMV, adenoviridae, papovaviridae, such as HPV, hepadna-viridae, such as HBV, infection by RNA viruses, such as picorvaviridae, especially polivirus and HAV, rhinoviruses and FMDV, togaviridae, flaviviridae, coronaviridae, paramyxo-viridae, such as RSV, orthomyoxoviridae, such as influenza virus, and retroviridae, especially HIV.

Combination Therapy

The methods, kits, and compositions of the invention may also include an antibiotic. For example, oxidatively transformed carotenoid, or a component thereof, may be administered with an antibiotic selected from, without limitation, aminoglycosides, such as amikacin, apramycin, arbekacin, bambermycins, butirosin, dibekacin, dihydrostreptomycin, fortimicin(s), fradiomycin, gentamicin, ispamicin, kanamycin, micronomicin, neomycin, neomycin undecylenate, netilmicin, paromomycin, ribostamycin, sisomicin, spectinomycin, streptomycin, streptonicozid, and tobramycin; amphenicols, such as azidamfenicol, chloramphenicol, chloramphenicol palmitate, chloramphenicol pantothenate, florfenicol, and thiamphenicol; ansamycins, such as rifampin, rifabutin, rifapentine, and rifaximin; β-Lactams, such as amidinocillin, amdinocillin, pivoxil, amoxicillin, ampicillin, aspoxicillin, azidocillin, azlocillin, bacampicillin, benzylpenicillinic acid, benzylpenicillin, carbenicillin, carfecillin, carindacillin, clometocillin, cloxacillin, cyclacillin, dicloxacillin, diphenicillin, epicillin, fenbenicillin, floxicillin, hetacillin, lenampicillin, metampicillin, methicillin, mezlocillin, nafcillin, oxacillin, penamecillin, penethamate hydriodide, penicillin G benethamine, penicillin G benzathine, penicillin G benzhydrylamine, penicillin G calcium, penicillin G hydragamine, penicillin G potassium, penicillin G, procaine, penicillin N, penicillin O, penicillin V, penicillin V benzathine, penicillin V hydrabamine, penimepicycline, phenethicillin, piperacillin, pivapicillin, propicillin, quinacillin, sulbenicillin, talampicillin, temocillin and ticarcillin; carbapenems, such as imipenem; cephalosporins, such as 1-carba (dethia) cephalosporin, cefactor, cefadroxil, cefamandole, cefatrizine, cefazedone, cefazolin, cefixime, cefinenoxime, cefodizime, cefonicid, cefoperazone, ceforanide, cefotaxime, cefotiam, cefpimizole, cefpirimide, cefpodoxime proxetil, cefroxadine, cefsulodin, ceftazidime, cefteram, ceftezole, ceftibuten, ceftizoxime, ceftriaxone, cefuroxime, cefuzonam, cephacetrile sodium, cephalexin, cephaloglycin, cephaloridine, cephalosporin, cephalothin, cephapirin sodium, cephradine, pivcefalexin, cephalothin, cefaclor, cefotetan, cefprozil, loracarbef, cefetamet, and cefepime; cephamycins such as cefbuperazone, cefmetazole, cefminox, cefetan, and cefoxitin; monobactams such as aztreonam, carumonam, and tigemonan; oxacephems such as flomoxef and moxolactam; lincosamides such as clindamycin and lincomycin; macrolides such as azithromycin, carbomycin, clarithromycin, erythromycin(s) and derivatives, josamycin, leucomycins, midecamycins, miokamycin, oleandomycin, primycin, rokitamycin, rosaramicin, roxithromycin, spiramycin and troleandomycin; polypeptides such as amphomycin, bacitracin, capreomycin, colistin, enduracidin, enylomycin, fusafungine, gramicidin(s), gramicidin S, mikamycin, polymyxin, polymyxin methanesulfonic acid, pristinamycin, ristocetin, teicoplanin, thiostrepton, tuberactinomycin, tyrocidine, tyrothricin, vancomycin, viomycin(s), virginiamycin and zinc bacitracin; tetracyclines such as spicycline, chlortetracycline, clomocycline, demeclocycline, doxycycline, guamecycline, lymecycline, meclocycline, methacycline, minocycline, oxytetracycline, penimepicycline, pipacycline, rolitetracycline, sancycline, senociclin and tetracycline; and 2,4-diaminopyrimidines such as brodimoprim, tetroxoprim and trimethoprim; nitrofurans such as furaltadone, furazolium, nifuradene, nifuratel, nifurfoline, nifurpirinol, nifurprazine, nifurtoinol and nitrofurantoin; quinolones such as amifloxacin, cinoxacin, ciprofloxacin, difloxacin, enoxacin, fleroxacin, flumequine, lomefloxacin, miloxacin, nalidixic acid, norfloxacin, ofloxacin, oxolinic acid, perfloxacin, pipemidic acid, piromidic acid, rosoxacin, temafloxacin, and tosufloxacin; sulfonamides such as acetyl sulfamethoxypyrazine, acetyl sulfisoxazole, azosulfamide, benzylsulfamide, chloramine-β, chloramine-T, dichloramine-T, formosulfathiazole, N2-formyl-sulfisomidine, N4-β-D-glucosylsulfanilamide, mafenide, 4'-(methyl-sulfamoyl)sulfanilanilide, p-nitrosulfathiazole, noprylsulfamide, phthalylsulfacetamide, phthalylsulfathiazole, salazosulfadimidine, succinylsulfathiazole, sulfabenzamide, sulfacetamide, sulfachlorpyridazine, sulfachrysoidine, sulfacytine, sulfadiazine, sulfadicramide, sulfadimethoxine, sulfadoxine, sulfaethidole, sulfaguanidine, sulfaguanol, sulfalene, sulfaloxic acid, sulfamerazine, sulfameter, sulfamethazine, sulfamethizole, sulfamethomidine, sulfamethoxazole, sulfamethoxypyridazine, sulfametrole, sulfamidochrysoidine, sulfamoxole, sulfanilamide, sulfanilamidomethanesulfonic acid triethanolamine salt, 4-sulfanilamidosalicyclic acid, N4-sulfanilylsulfanilamide, sulfanilylurea, N-sulfanilyl-3,4-xylamide, sulfanitran, sulfaperine, sulfaphenazole, sulfaproxyline, sulfapyrazine, sulfapyridine, sulfasomizole, sulfasymazine, sulfathiazole, sulfathiourea, sulfatolamide, sulfisomidine and sulfisoxazole; sulfones, such as acedapsone, acediasulfone, acetosulfone, dapsone, diathymosulfone, glucosulfone, solasulfone, succisulfone, sulfanilic acid, p-sulfanilylbenzylamine, p,p'-sulfonyldianiline-N,N' digalactoside, sulfoxone and thiazolsulfone; lipopeptides such as daptomycin; oxazolidones such as linezolid; ketolides such as telithromycin; and miscellaneous antibiotics such as clofoctol, hexedine, magainins, methenamine, methenamine anhydromethylene-citrate, methenamine hippurate, methenamine mandelate, methenamine sulfosalicylate, nitroxoline, squalamine, xibomol, cycloserine, mupirocin, and tuberin. The use of oxidatively transformed carotenoid, or a component thereof, in combination with an antibiotic therapy can be desirable to enhance the efficacy of an antibiotic to resistant strains of a microbe, to reduce the likelihood of forming resistant strains of a microbe while undergoing treatment with an antibiotic, and/or to reduce antibiotic load. This can be achieved by enhancing the host immune response to the microbe with oxidatively transformed carotenoid, or a component thereof.

Administration and Formulation

The invention features compositions, kits, and methods for sensitizing the innate and adaptive immune system of a subject to an infection. For oxidatively transformed carotenoid, typical dose ranges are from about 5 µg/kg to about 50 mg/kg of body weight per day. Desirably, a dose of between 5 µg/kg and 5 mg/kg of body weight, or 5 µg/kg and 0.5 mg/kg of body weight, is administered. For a component of oxidatively transformed carotenoid, typical dose ranges are from about 0.05 µg/kg to about 500 µg/kg of body weight per day. Desirably, a dose of between 0.05 µg/kg and 50 µg/kg of body weight, or 0.05 µg/kg and 5 µg/kg of body weight, is administered. The dosage of oxidatively transformed carotenoid, or a component thereof, to be administered is likely to depend on such variables as the species, diet, and age of the animal. Standard trials, such as those described in Example 1 may be used to optimize the dose and dosing frequency of the oxidatively transformed carotenoid or a component thereof.

Oxidatively transformed carotenoid, or a component thereof, may be administered to humans, domestic pets, livestock, or other animals with a pharmaceutically acceptable diluent, carrier, or excipient. Administration may be topical, parenteral, intravenous, intra-arterial, subcutaneous, intramuscular, intracranial, intraorbital, ocular, intraventricular, intracapsular, intraspinal, intracisternal, intraperitoneal, intranasal, aerosol, by suppositories, or oral administration. In certain formulations the oxidatively transformed carotenoid, or a component thereof, is provided in unit dosage form.

Therapeutic formulations may be in the form of liquid solutions or suspensions; for oral administration, formulations may be in the form of tablets or capsules; and for intranasal formulations, in the form of powders, nasal drops, ear drops, or aerosols.

Methods well known in the art for making formulations are found, for example, in "Remington: The Science and Practice of Pharmacy" (20th ed., ed. A. R. Gennaro, 2000, Lippincott Williams & Wilkins). Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Nanoparticulate formulations (e.g., biodegradable nanoparticles, solid lipid nanoparticles, liposomes) may be used to control the biodistribution of the compounds. Other potentially useful parenteral delivery systems include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycholate and deoxycholate, or may be oily solutions for administration in the form of nasal drops, or as a gel. The concentration of the compound in the formulation will vary depending upon a number of factors, including the dosage of the drug to be administered, and the route of administration.

Administration of compounds in controlled release formulations is useful where the compound of formula I has (i) a narrow therapeutic index (e.g., the difference between the plasma concentration leading to harmful side effects or toxic reactions and the plasma concentration leading to a therapeutic effect is small; generally, the therapeutic index, TI, is defined as the ratio of median lethal dose (LD50) to median effective dose (ED50)); (ii) a narrow absorption window in the gastro-intestinal tract; or (iii) a short biological half-life, so that frequent dosing during a day is required in order to sustain the plasma level at a therapeutic level.

Many strategies can be pursued to obtain controlled release in which the rate of release outweighs the rate of metabolism of the therapeutic compound. For example, controlled release can be obtained by the appropriate selection of formulation parameters and ingredients, including, e.g., appropriate controlled release compositions and coatings. Examples include single or multiple unit tablet or capsule compositions, oil solutions, suspensions, emulsions, microcapsules, microspheres, nanoparticles, patches, and liposomes.

Formulations for oral use include tablets containing the active ingredient(s) in a mixture with non-toxic pharmaceutically acceptable excipients. These excipients may be, for example, inert diluents or fillers (e.g., sucrose and sorbitol), lubricating agents, glidants, and antiadhesives (e.g., magnesium stearate, zinc stearate, stearic acid, silicas, hydrogenated vegetable oils, or talc).

Formulations for oral use may also be provided in unit dosage form as chewable tablets, tablets, caplets, or capsules (i.e., as hard gelatin capsules wherein the active ingredient is mixed with an inert solid diluent, or as soft gelatin capsules wherein the active ingredient is mixed with water or an oil medium).

Oxidatively transformed carotenoid, or a component thereof, may be formulated with a pharmaceutically acceptable diluent, carrier, or excipient as described in U.S. Ser. No. 10/196,695, published May 22, 2003.

Oral Hygiene Formulations

The oxidatively transformed carotenoid, or a component thereof, can be formulated as a mouthwash or toothpaste useful for general oral hygiene and, specifically, to kill the microbes that cause plaque, gingivitis, and bad breath. The concentration of the oxidatively transformed carotenoid, or a component thereof, can be from 0.0001 to 1 w/w %, more preferably from 0.001 to 0.1 w/w %.

The mouthwashes of the invention can be prepared by simply combining oxidatively transformed carotenoid, or a component thereof, with an existing mouthwash. Optionally, the mouthwashes of the invention further include water, fluoride, flavorings, alcohol, hydrogen peroxide, thymol, eucalyptol, hexetidine, methyl salicylate, menthol, chlorhexidine gluconate, benzalkonium chloride, cetylpyridinium chloride, methylparaben, hydrogen peroxide, domiphen bromide, enzymes, calcium, zinc, and/or sweeteners (i.e., sorbitol, sucralose, or sodium saccharine).

The toothpastes of the invention can be prepared by simply combining oxidatively transformed carotenoid, or a component thereof, with an existing toothpaste. Optionally, the toothpastes of the invention further include fluoride (i.e., sodium fluoride or sodium monofluorophosphate), a remineralizing agent (i.e., hydroxyapatite, amorphous calcium phosphate, calcium carbonate), a foaming agent (i.e., sodium lauryl sulfate), sodium carbonate, enzymes, vitamins, herbs, calcium, calcium sodium phosphosilicate, hydrogen peroxide, an antibacterial agent (triclosan, zinc chloride), a thickener (i.e., glycerin), and/or flavorings (i.e., spearmint, peppermint, regular mint, etc).

Ophthalmic Formulations

The ophthalmic pharmaceutical compositions of the invention can be prepared by addition of oxidatively transformed carotenoid, or a component thereof, to an existing ophthalmic formulation. Optionally the ophthalmic pharmaceutical composition includes buffers, surfactants, stabilizers, preservatives, ophthalmic wetting agents, and/or ophthalmic diluting agents. Wetting agents commonly used in ophthalmic solutions include carboxymethylcellulose, hydroxypropyl methylcellulose, glycerin, mannitol, polyvinyl alcohol or hydroxyethylcellulose and the diluting agent may be water, distilled water, sterile water, or artificial tears, wherein the wetting agent is present in an amount of about 0.001% to about 10%. The concentration of the oxidatively transformed carotenoid, or a component thereof, can be from 0.0001 to 1 w/w %, more preferably from 0.001 to 0.1 w/w %. The ophthalmic composition can be used for treatment of an infection (i.e., a bacterium, a virus, a fungus, or an amoeba, or a parasite) of the eye, resulting in, for example, conjunctivitis, corneal abrasion, ulcerative infectious keratitis, epithelial keratitis, stromal keratitis, or herpesvirus-related keratitis.

Examples of ophthalmic solutions and ophthalmic ointments can be formulated into such preparations utilizing a number of widely-used methods well known to those of ordinary skill in the art. In the case of ophthalmic solutions, for example, they can be prepared using distilled water, an aqueous base, or any other acceptable base; tonicity agents such as sodium chloride and concentrated glycerol; buffers such as sodium phosphate and sodium acetate; surfactants such as polyoxyethylene sorbitan monooleate, stearic polyoxyl 40, and polyoxyethylene hydrogenated castor oil; stabilizers such as sodium citrate and sodium edetate; preservatives such as benzalkonium chloride, thimerosal, chlorobutanol, sodium chloride, boric acid, parahydroxybenzoic acid esters (sorbate, benzoate, propionate), chlorobutanol, benzyl alcohol, mercurials, paraben; etc., and mixtures thereof, if necessary. Benzalkonium chloride and thimerosal are the preferred preservatives. The ophthalmic formulation may be varied to include acids and bases to adjust the pH; tonicity imparting agents such as sorbitol, glycerin and dextrose; other viscosity imparting agents such as sodium carboxymethylcellulose, microcrystalline cellulose, polyvinylpyrrolidone, polyvinyl alcohol and other gums; suitable absorption enhancers, such as surfactants, bile acids; stabilizing agents such as antioxidants, like bisulfites and ascorbates; metal chelating agents, such as sodium edetate; and drug solubility enhancers, such as polyethylene glycols. These additional ingredients help make commercial solutions with adequate stability so that they need not be compounded on demand.

The ophthalmic formulation of the invention can be a sterile aqueous carrier, a salve, or an ointment. Salves and ointments typically include oxidatively transformed carotenoid, or a component thereof, dissolved or suspended in a sterile pharmaceutically acceptable salve or ointment base, such as a mineral oil-white petrolatum base. In salve or ointment compositions, anhydrous lanolin may also be included in the formulation. Thimerosal or chlorobutanol can be added to the formulation as antimicrobial agents.

The following examples are put forth so as to provide those of ordinary skill in the art with a complete disclosure and description of how the methods and compositions claimed herein are performed, made, and evaluated, and are intended to be purely exemplary of the invention and are not intended to limit the scope of what the inventors regard as their invention.

Example 1. Evaluation of Monocyte Cytokine Profiles Following Supplementation with Oxidatively Transformed Carotenoid (OxBC)

The following results demonstrate that OxBC activates cytokine responses in mononuclear phagocytes. Oxidatively transformed carotenoid has the ability to prime cells to respond to challenge, such as invading pathogens, and to enhance antimicrobial activities in challenged cells.

Inflammation, a major component of nonspecific immunity, is a complex sequence of events that forms the primary physiologic process by which the body repairs tissue damage and defends against infectious, toxic or allergenic agents. Although the precise mechanisms controlling the induction and propagation of pro-inflammatory responses remain largely unclear, chemokines and soluble mediators released from resident immune cells represent the primary mediators. Numerous studies have shown that micronutrients such as β-carotene can significantly impact on diverse macrophage functions, including their contribution to overt inflammatory responses, by activating the production of cytokines and other pro-inflammatory mediators. Thus, we evaluated the effect of OxBC on the production of proinflammatory (tumor necrosis factor (TNF)-α, interleukin (IL)-1β, IL-6 and interferon (IFN)-γ) and immunoregulatory (IL-12, IL-8 and monocyte chemoattractant protein (MCP)-1) cytokines by human monocytes and lymphocytes.

Methods:

Compound Preparation:

OxBC was prepared from β-carotene (see U.S. Pat. No. 5,475,006) and stored at −20° C. prior to use. Stock solutions (50 mM of carotene equivalents) were prepared by dissolving 26.85 mg OxBC/ml DMSO and stored as 500 µl aliquots at −80° C. Working 200 µM solutions of OxBC were prepared by dilution in the appropriate culture media and sterilized by filtration (0.22 µm pore size). The equivalent values of OxBC tested and the associated amount of DMSO in both test and control samples are indicated in Table 1. Equivalent amounts of DMSO vehicle were used as controls.

TABLE 1

Concentrations of OxBC and associated DMSO values

| OxBC (µM) | OxBC (µg/ml) | DMSO (%, v/v) |
|---|---|---|
| 0.0 | 0.00 | 0.000 |
| 0.1 | 0.05 | 0.001 |
| 0.5 | 0.27 | 0.005 |
| 1.0 | 0.54 | 0.010 |
| 2.5 | 1.34 | 0.025 |
| 5.0 | 2.67 | 0.050 |
| 10 | 5.38 | 0.100 |
| 15 | 8.01 | 0.150 |
| 25 | 13.4 | 0.250 |
| 50 | 26.9 | 0.500 |

Cell Lines

Human THP-1 monocytoid cells (acute monocytic leukemia) were obtained from American Type Tissue Collection (#TIB-202). Cells were cultured in RPMI-1640 medium supplemented with 2 mM L-glutamine, 10 mM HEPES, 1.0 mM sodium pyruvate, 10% fetal bovine serum and antibiotics. Peripheral blood monocytes (PBM) and lymphocytes (PBL) were isolated from PBMC by positive and negative selection, respectively, using the Miltenyi Biotec MACs magnetic separation system. PBM were cultured in RPMI-1640 medium supplemented with 2 mM L-glutamine, 10 mM HEPES, 1.0 mM sodium pyruvate, 20% fetal bovine serum and antibiotics. PBL were seeded in the same medium with the exception that 10% FBS was used. Specific cell densities and experimental conditions are described below.

Experimental Conditions

Cells were evaluated in both naïve challenge and LPS challenge models. For naive studies, cells were exposed directly to OxBC for varying time frames and cytokine expression evaluated in conditioned medium (CM) by ELISA. For LPS challenge, cells were first incubated with OxBC for the indicated time, at which point OxBC was removed and replaced with fresh medium lacking the compound. At different time points post-treatment, cells were then challenged with LPS (15 ng/ml) for 24 h prior to cytokine levels in CM being evaluated by ELISA. In a variation of the LPS challenge scenario, primary PBM were first challenged with LPS for 24 h. After this initial stimulation, LPS-treated cells were then exposed to OxBC for 24 h before CM was harvested for ELISA analysis.

Enzyme-Linked Immunosorbent Assay (ELISA)

Analysis of cytokine levels in CM was performed using Endogen Human ELISA kits (Pierce) according to manufacturer's instructions. CM was prepared by centrifugation to remove cellular debris and either used neat, diluted with complete medium or concentrated using Nanosep 3K centrifugal concentrators (Pall) to ensure that cytokine levels fell within the linear ranges of each assay. Where appropriate, samples were stored at −80° C. and thawed by gradual equilibration at room temperature prior to use. Briefly, 50 µl samples were added to each well of a microplate to which antibody specific to the cytokine of interest had been adsorbed and incubated at room temperature for 1-3 h. Plates were washed three times to remove nonspecifically bound material and incubated for an additional 1-3 h with biotinylated antibody specific to the cytokine of interest. After washing, plates were incubated for 30 min with steptavidin-horse radish peroxidase reagent followed by an additional washing cycle. Washed plates were incubated for 30 min with 3,3',5,5'-tetramethylbenzidine (TMB) substrate, the reaction stopped and absorbance measured at 450 nm (550 nm reference). Reference curves were generated for each cytokine using the supplied recombinant standard.

Results and Discussion

A primary proof-of-principle study was conducted in THP-1 cells that were untreated (mock) or treated for 24 h with OxBC, PMA (25 ng/ml) and vehicle (DMSO). Direct stimulation with OxBC had no perceivable effect on inflammatory cytokine levels (see Table 2), although moderate increases in the regulatory cytokines MCP-1 and IL-8 were detectable. These studies were expanded to include OxBC over a range of concentrations (2.5, 7.5 and 12.5 µM) and concentration of samples in an attempt to increase detection of less abundant cytokines. OxBC at 12.5 µM was found to induce increased expression of MCP-1 (58.1±8.8%) and IL-8 (42.1±1.0%), but not the levels of other cytokines (see Table 3). Moreover, no change in MCP-1 and IL-8 expression was detected at lower concentrations of the compound. Both MCP-1 and IL-8 function as cytokines to recruit immune cells to sites of infection or injury. For example, IL-8 primarily recruits neutrophils within an inflammatory response and is also termed neutrophils recruitment factor (NRF), while MCP-1 primarily functions to recruit other monocytes. Expression of either cytokine by monocytes/macrophages is induced in response to detection of antigen or phagocytosis of an invading pathogen.

TABLE 2

Proof-of-principle cytokine release assays

| Cytokine | OxBC (12.5 µM) | PMA (25 ng/ml) | DMSO | Mock[1] |
|---|---|---|---|---|
| Inflammatory | | | | |
| TNF | 31.5 ± 3.0 | 110.1 ± 1.7 | 32.1 ± 1.1 | 32.0 ± 1.6 |
| IL-1β | 9.7 ± 0.2 | 73.4 ± 2.8 | 6.7 ± 0.0 | 7.1 ± 0.4 |
| IL-6 | ND[2] | ND | ND | ND |
| IFNγ | 9.6 ± 0.0 | 10.0 ± 1.3 | 10.4 ± 0.5 | 5.6 ± 0.3 |
| Regulatory | | | | |
| IL-8 | 52.7 ± 2.8 | 637.2 ± 18.6 | 32.3 ± 0.7 | 41.1 ± 2.1 |
| IL-12 | 9.1 ± 2.1 | 8.0 ± 6.5 | 7.6 ± 3.4 | 7.5 ± 0.4 |
| MCP-1 | 164.5 ± 43.3 | 654.9 ± 60.2 | 80.8 ± 34.4 | 61.7 ± 3.8 |

[1]Values represent pg/ml as determined by reference standards included in each assay.
[2]ND, not detected; value was less than 5.0 pg/ml

TABLE 3

Cytokine profiles following OxBC treatment

| Sample | Conc. | TNF | IL-1β | IL-6 | IFNγ | IL-8 | IL-12 | MCP-1[1] |
|---|---|---|---|---|---|---|---|---|
| OxBC | 2.5 µM | 31.3 | 14.5 | ND[2] | 21.1 | 42.5 | 20.1 | 79.6 |
| | 7.5 µM | 31.4 | 13.8 | ND | 21.2 | 40.3 | 18.2 | 85.6 |
| | 12.5 µM | 36.1 | 14.7 | ND | 23.9 | 61.4 | 19.6 | 104.0 |
| DMSO[3] | 2.5 µM | 37.3 | 15.1 | ND | 21.9 | 47.4 | 21.4 | 71.1 |
| | 7.5 µM | 36.0 | 13.7 | ND | 21.3 | 42.3 | 21.0 | 72.8 |
| | 12.5 µM | 38.7 | 14.0 | ND | 22.2 | 43.2 | 21.5 | 65.8 |
| PMA | 25 ng/ml | 108.5 | 62.5 | 20.3 | 24.9 | 712.4 | 20.9 | 574.8 |

[1]Values represent pg/ml as determined by reference standards included in each assay.
[2]ND, not detected; value was less than 5.0 pg/ml
[3]DMSO values represent amount of vector for the corresponding concentration of OxBC indicated.

Given that OxBC exhibited limited effects on inflammatory cytokine expression when naïve monocytoid cells were challenged, we next evaluated the potential for the compound to alter monocyte responses to proinflammatory stimuli, namely lipopolysaccharide (LPS). To evaluate this potential, a secondary proof-of-principle study was conducted in which THP-1 cells were pretreated with OxBC (0.1, 0.5, 1.0 µM) for 24 h, cultured for 5 days and then stimulated with LPS for an additional 24 h before TNF expression was measured by ELISA. Lower concentrations of OxBC were selected to more closely model availability within a host, while TNF was selected as the prototypical proinflammatory cytokine. As shown in Table 4, pretreatment with OxBC upregulated TNF expression following LPS challenge by approximately 25% at all concentrations evaluated. These studies were subsequently extended to other proinflammatory cytokines using a similar prime and challenge model. Increased IL-6 and IL-1β, but not IFNγ, expression was detected when cells were primed with either 0.1 or 0.5 µM of OxBC (see Table 5). Of interest, no change in cytokine expression was observed at 1.0 µM of the compound. IL-6 is one of the most important mediators of fever of acute phase response; however, the cytokine is also required for maintaining microbial resistance. Both TNF and IL-1β are pivotal pleiotropic cytokines in innate immune and inflammatory responses that regulate the function of phagocytes and lymphocytes. Similarly, OxBC pretreatment was also found to upregulate expression of the regulatory cytokine IL-8 following LPS challenge. Specifically, IL-8 expression was increased by 33±4% and 49±5% following pretreatment with 0.1 and 0.5 µM of OxBC, respectively, compared to cells stimulated with LPS alone. No difference was observed in cultures pretreated with 1 µM of the compound, however.

TABLE 4

TNF expression following OxBC prime and LPS challenge (proof of principle)

| Sample | Concentration | TNF[1] | Fold Change[2] |
|---|---|---|---|
| OxBC (µM) | 0.1 | 60.4 ± 2.1 | |
| | 0.5 | 61.1 ± 1.7 | |
| | 1.0 | 64.6 ± 5.2 | |
| OxBC (µM) + LPS (15 ng/ml) | 0.1 | 1840.4 ± 2.6 | 1.25 ± 0.1 |
| | 0.5 | 1845.5 ± 7.3 | 1.25 ± 0.1 |
| | 1.0 | 1832.0 ± .4 | 1.24 ± 0.1 |
| LPS (ng/ml) | 15 | 1471.2 ± 171.2 | 1.00 ± 0.1 |

[1]Values represent pg/ml as determined by reference standards included in each assay.
[2]Fold change relative to cells treated with LPS alone.

TABLE 5

Proinflammatory cytokine expression following OxBC prime and LPS challenge

| | | IL-6 | | IL-1β | | IFNγ | |
|---|---|---|---|---|---|---|---|
| Sample | Conc | pg/ml | fold[1] | pg/ml | fold | pg/ml | fold |
| OxBC (µM) | 0.1 | ND | | 54.7 ± 16.6 | | 18.0 ± 2.1 | |
| | 0.5 | ND | | 57.3 ± 0.1 | | 20.0 ± 5.3 | |
| | 1.0 | ND | | 49.9 ± 7.0 | | 22.0 ± 1.1 | |
| OxBC (µM) + LPS (15 ng/ml) | 0.1 | 49.4 ± 3.9 | 1.31 | 1424.8 ± 117.1 | 1.19 | 21.0 ± 0.1 | 1.00 |
| | 0.5 | 56.1 ± 2.8 | 1.48 | 1668.6 ± 77.9 | 1.40 | 20.5 ± 2.7 | 0.98 |
| | 1.0 | 37.8 ± 2.2 | 1.00 | 1065.2 ± 94.5 | 0.89 | 19.4 ± 3.7 | 0.93 |
| LPS (ng/ml) | 15 | 37.7 ± 1.9 | 1.00 | 1194.0 ± 45.7 | 1.00 | 20.9 ± 0.6 | 1.00 |

[1]Fold change relative to cells treated with LPS alone.

Figure 2:
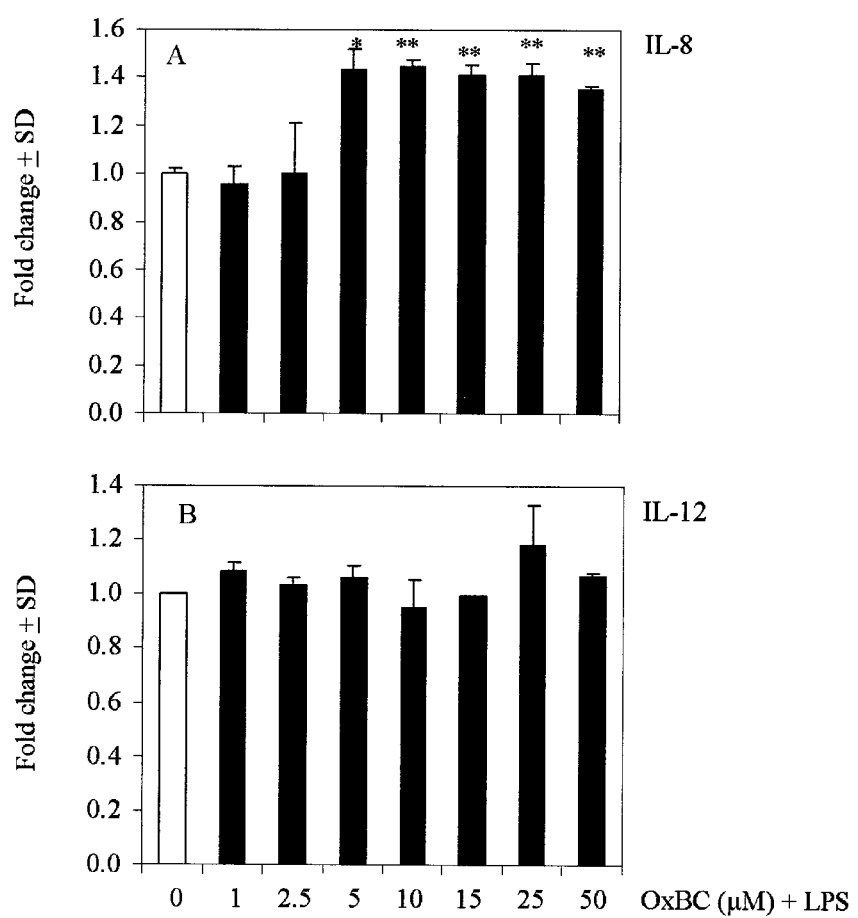
FIG. 2 is a graph depicting IL-8 (A) and IL-12 (B) levels in primary PBM incubated with LPS prior to being treated with OxBC. Primary PBM were incubated with LPS (15 ng/ml) for 24 h prior to being treated with the indicated concentrations of OxBC. After 24 h, CM was harvested and IL-8 (A) and IL-12 (B) levels detected by ELISA (* $p<0.05$, ** $p<0.01$, Students t-test). Expression of regulatory cytokine IL-8 was elevated in human monocytes exposed to OxBC after the challenge with LPS, suggesting that OxBC has an ability to increase antimicrobial activity.

Because monocytes are the effector cell of the innate immune response of greatest interest, we next evaluated whether OxBC could influence inflammatory cytokine expression in primary PBM that had previously been exposed to LPS challenge. PBM were initially treated for 24 h with LPS (15 ng/ml) and then stimulated for an additional 24 h with varying concentrations of OxBC before CM was collected for ELISA analysis. No change in IL-6 expression was detected following OxBC treatment, while TNF levels were elevated (approximately 25%) only at lower concentrations of the compound (see FIG. 1). However, IL-1β expression was consistently elevated at OxBC concentrations greater than 5 µM, with maximal increases of approximately 50% detected (FIG. 1). Evaluation of the regulatory cytokines, IL-8 and IL-12, revealed that although no change in IL-12 expression was observed in cells pretreated with OxBC, IL-8 expression was significantly elevated relative to untreated monocytes at concentrations of OxBC exceeding 2.5 µM (FIG. 2).

Example 2. Evaluation of the Expression of Immune-Relevant Surface Receptors on Monocytes Following Oxidatively Transformed Carotenoid (OxBC) Treatment The following results demonstrate that OxBC treatment is associated with increased expression of CD14, CD51, CD16 and CD36, all differentiation markers involved in the activation of monocytes. Moreover, increased expression of the lymphocyte costimulatory molecules CD86 (i.e., B7) and CD40L was also observed, suggesting the capacity to activate both the innate and adaptive arms of the immune system. In LPS challenge models when monocytes were primed with lower concentrations of OxBC, little change in differentiation marker levels was detected. However, OxBC treatment was associated with increased expression of costimulatory surface receptors in response to LPS challenge.

Undifferentiated monocytes lose their small, rounded morphology and exhibit increased size, cell spreading, and granularity as they differentiate into macrophages. Several differentiation antigens have also been identified in monocytes and associated with a variety of biological functions related to innate and specific immunity. The expression profile of these surface antigens changes as monocytes differentiate, providing a means of quantifying the number of mature macrophages in a mixed population by flow cytometry. For these studies, differentiation and innate function were evaluated by assessing levels of representative surface moieties that function in such processes as cell adhesion (integrins CD11b/CD18 and CD51), the binding of microbial components (CD14, LPS receptor), scavenging and phagocytosis (CD36) and cell-mediated immune responses (CD16, low affinity IgG receptor required for antibody-dependent cell killing). Typically, these receptors are expressed at lower levels on naïve monocytes and are upregulated upon stimulation. To evaluate the influence of OxBC on the adaptive immune functions of monocytes, surface expression of the MHC class II molecules, HLA-DR and HLA-DP, were evaluated. These molecules are the characteristic monocyte cell surface markers involved in antigen presentation. Similarly, expression of other cell surface molecules with roles in antigen presentation to T-cells, including the costimulatory leukocyte antigens B7-2 (CD86), CD40 and CD40L were determined.

Methods

Compound Preparation

OxBC stocks were prepared as described in Example 1.

Cell Lines and Conditions

Human THP-1 monocytoid cells (acute monocytic leukemia) were obtained from American Type Tissue Collection (#TIB-202). Cells were cultured in RPMI-1640 medium supplemented with 2 mM L-glutamine, 10 mM HEPES, 1.0 mM sodium pyruvate, 10% fetal bovine serum and antibiotics. Cells were seeded ($5 \times 10^5$ cells/well, 6-well culture plates) 24 h prior to treatment with OxBC and harvested for analysis according to three protocols: 1) Cells were treated with OxBC (2.5, 7.5 or 12.5 µM) for 24 h and than evaluated for surface receptor expression; 2) Cells were treated with OxBC (0.1, 0.5 or 1.0 µM) for 24 h, at which point fresh media lacking OxBC was supplied for 48 h prior to analysis, and 3) Cells were treated with OxBC (0.1, 0.5 or 1.0 µM) for 24 h, at which point fresh media lacking OxBC was supplied for 5 days. Treated cells were then stimulated with LPS (15 ng/ml) for 24 h prior to analysis. Cells incubated in an equivalent percentage (v/v) of DMSO alone served as controls. For studies in which LPS stimulation was not employed, PMA 25 ng/ml) was used as positive stimulator of monocytes differentiation.

FACS Analysis

Phycoerythrin (PE)-labeled primary antibodies against human CD11b, CD14, CD16, CD36, CD51/CD61, HLA (broad isoforms), HLA-$B_7$, CD86, CD40, CD40L and CD3 were obtained from AbCam. Receptor expression was evaluated using direct immunofluorescence labeling and flow cytometry analysis. Briefly, triplicate cell aliquots in cold buffer (PBS containing 10% FBS and 1% sodium azide) were incubated with primary antibody (10-20 µl) for 45 min at room temperature under low light conditions. Cells were washed three times and resuspended in 500 µl of buffer for analysis using a FacsAria cell sorter. Unlabeled cells and cells labeled with antibody alone served as controls.

Results and Discussion

Figure 3:
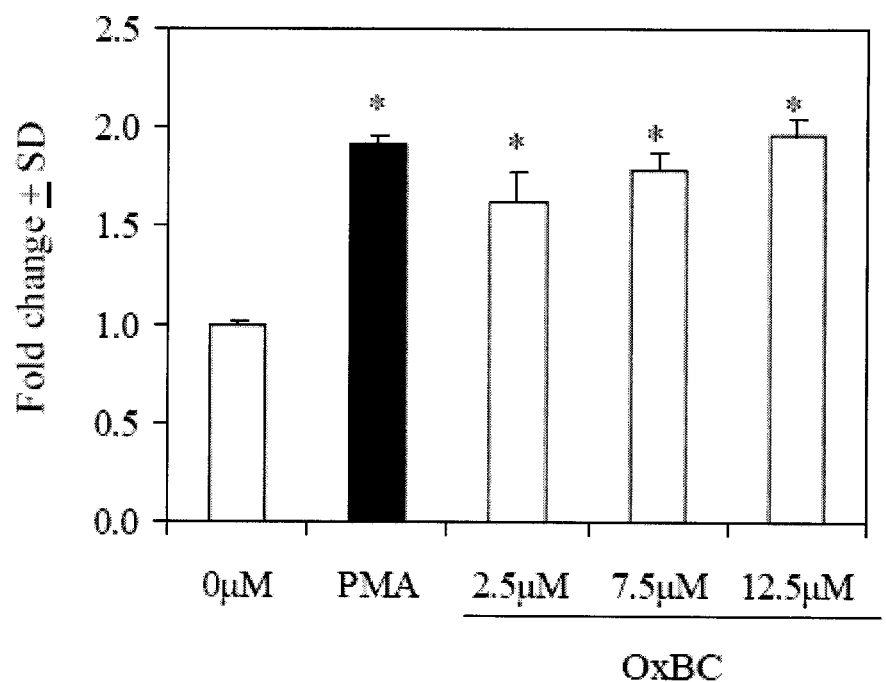
FIG. 3 is a graph depicting CD14 expression in OxBC-treated THP-1 cells. THP-1 monocytes were incubated with the indicated concentration of OxBC or DMSO control. FACS analysis was performed at 24 h post-treatment. Values represent fold changes relative to DMSO controls. Phorbol myristate acetate (PMA) was used at 25 ng/ml (* $p<0.001$, Student's t-test versus DMSO controls). OxBC promotes expression of CD14, a receptor that binds to microbial component, and primes the innate immune response to infection.

THP-1 cells were treated with OxBC for 24 h and the expression of differentiation antigens evaluated by direct-labeled flow cytometry. As shown in Table 6 and FIG. 3, the most striking characteristic of OxBC treatment was upregulated expression of the prototypical monocyte differentiation antigen, CD14, over the range of concentrations evaluated. This effect was dose-dependent and peaked at a 2-fold increase when 12.5 µM of OxBC was used, a result comparable to the effect of PMA. CD14 is a membrane-associated glycoprotein that acts as a coreceptor with Toll-like receptor (TLR)-4 to detect bacterial LPS. In doing so, it plays a pivotal role in mediating the innate immune response bacterial infections, including cytokine secretion and the inflammatory response. Thus, its upregulation by OxBC indicated that the compound possessed the ability to activate a fundamental innate pathway. In addition to CD14, upregulated expression of CD51 (37%), an integrin involved in monocyte adhesion to endothelial cells following activation, and CD16 (39%), an Fc receptor that recognizes antibodies to support antibody-guided cell killing, was detected at the 12.5 µM concentration of OxBC. Taken together, these results provided evidence that OxBC could exert a differentiation stimulus in monocytoid cells. It should be noted that staining with CD3, a lymphocyte marker, as a control indicated that the THP-1 cells did not express the receptor (data not shown).

CD11b, an integrin preferentially expressed in myeloid cells whose engagement generates signals leading to monocyte activation and proinflammatory cytokine release, and CD36, a surface moiety associated with the initiation of phagocytosis, are constitutively expressed on monocytoid cells at levels approaching uniformity. Thus, we also evaluated fluorescence intensity following staining for these molecules as a measure of receptor density. This was done to avoid missing potential effects that would otherwise be dampened by the abundance of positively-labeled cells. As shown in Table 7, CD36 expression is increased by approximately 27% following treatment with 12.5 of OxBC, while CD11b levels were increased to a small degree. In comparison, PMA increased the densities of both receptors by a far greater margin, ranging from 2 to 4-fold.

TABLE 7

| Receptor densities | | |
|---|---|---|
| Treatment | CD11b[1] | CD36 |
| OxBC (µM) | | |
| 0.0 | 1.00 ± 0.01 | 1.00 ± 0.02 |
| 2.5 | 0.96 ± 0.04 | 0.96 ± 0.02 |
| 7.5 | 1.17 ± 0.01 | 1.14 ± 0.01 |
| 12.5 | 1.11 ± 0.01 | 1.27 ± 0.01 |
| PMA[2] | 1.97 ± 0.01 | 4.57 ± 0.03 |

[1]Values represent fold changes (± SD) relevant to vehicle controls. Bold indicates statistical significance.
[2]PMA was used at 25 ng/ml as a control for positive stimulus.

Figure 4:
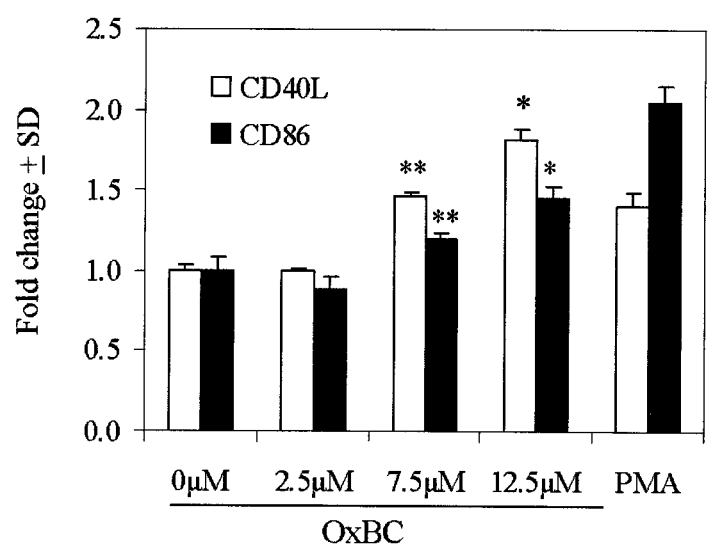
FIG. 4 is a graph depicting CD40L and CD86 expression in OxBC-treated THP-1 cells. THP-1 monocytes were incubated with the indicated concentration of OxBC or DMSO control. FACS analysis was performed at 24 h post-treatment. Values represent fold changes relative to DMSO controls. PMA was used at 25 ng/ml (* $p<0.005$, ** $p<0.001$, Student's t-test versus DMSO controls). OxBC increased expression of surface receptors involved in antigen presentation and the stimulation of lymphocyte response therefore increasing activity of monocytes to respond to immune challenge.

The expression of surface receptors involved in antigen presentation and the stimulation of lymphocyte response were also evaluated by flow cytometry. Expression of HLA B7-2 (aka CD86) and CD40L was upregulated by treatment with 7.5 and 12.5 µM of OxBC (Table 8, FIG. 4). CD86 provides a costimulatory signal required for T-cell activation by macrophages through its interaction with CD28. This interaction primes effector T cells to respond against antigens presented by activated macrophages. CD40L, or CD154, is a member of the TNF superfamily that binds to CD40 on antigen presenting cells and serves as a costimulatory molecule. CD40L is most abundant expressed on $CD4^+$ T lymphocytes; however, recent findings have demonstrated that CD40L is also expressed on other immune effector cells, including monocytes/macrophages, where it serves to increase the level of activation of macrophages and enhance phagocytotic and cytokine producing activities. Thus, like CD14, these two molecules act to increase the capacity of activated monocytes to respond to immune challenge.

TABLE 6

| Differentiation antigen expression in THP-1 cells | | | | | |
|---|---|---|---|---|---|
| Treatment | CD11b[1] | CD51 | CD14 | CD36 | CD16 |
| OxBC (µM) | | | | | |
| 0.0 | 1.00 ± 0.01 | 1.00 ± 0.07 | 1.00 ± 0.03 | 1.00 ± 0.14 | 1.00 ± 0.05 |
| 2.5 | 1.01 ± 0.04 | 1.13 ± 0.05 | 1.62 ± 0.16 | 0.99 ± 0.01 | 1.09 ± 0.09 |
| 7.5 | 1.01 ± 0.01 | 1.15 ± 0.02 | 1.79 ± 0.09 | 1.02 ± 0.01 | 0.95 ± 0.06 |
| 12.5 | 1.00 ± 0.01 | 1.37 ± 0.08 | 1.97 ± 0.07 | 1.03 ± 0.01 | 1.39 ± 0.11 |
| PMA[2] | 0.97 ± 0.02 | 5.07 ± 0.29 | 1.91 ± 0.06 | 1.03 ± 0.01 | 4.77 ± 0.31 |

[1]Values represent fold changes (± SD) relevant to vehicle controls. Bold indicates statistical significance.
[2]PMA was used at 25 ng/ml as a control for positive stimulus.

TABLE 8

Expression of costimulatory molecules on THP-1 monocytes.

| Treatment | HLA[1] (DQ/DR/DP) | B7-2 (CD86) | CD40L | CD40 counts | CD40 intensity |
|---|---|---|---|---|---|
| OxBC (μM) | | | | | |
| 0.0 | 1.00 ± 0.03 | 1.00 ± 0.09 | 1.00 ± 0.04 | 1.00 ± 0.04 | 1.00 ± 0.01 |
| 2.5 | 1.19 ± 0.03 | 0.88 ± 0.08 | 0.99 ± 0.02 | 1.00 ± 0.01 | 1.14 ± 0.03 |
| 7.5 | 1.19 ± 0.01 | 1.20 ± 0.05 | 1.46 ± 0.03 | 1.00 ± 0.01 | 1.01 ± 0.01 |
| 12.5 | 1.02 ± 0.01 | 1.45 ± 0.08 | 1.82 ± 0.05 | 0.99 ± 0.01 | 0.93 ± 0.01 |
| PMA[2] | 1.05 ± 0.01 | 2.04 ± 0.29 | 1.4 ± 0.10 | 0.98 ± 0.01 | 1.31 ± 0.1 |

[1]Values represent fold changes (± SD) relevant to vehicle controls. Bold indicates statistical significance.
[2]PMA was used at 25 ng/ml as a control for positive stimulus.

Figure 5:
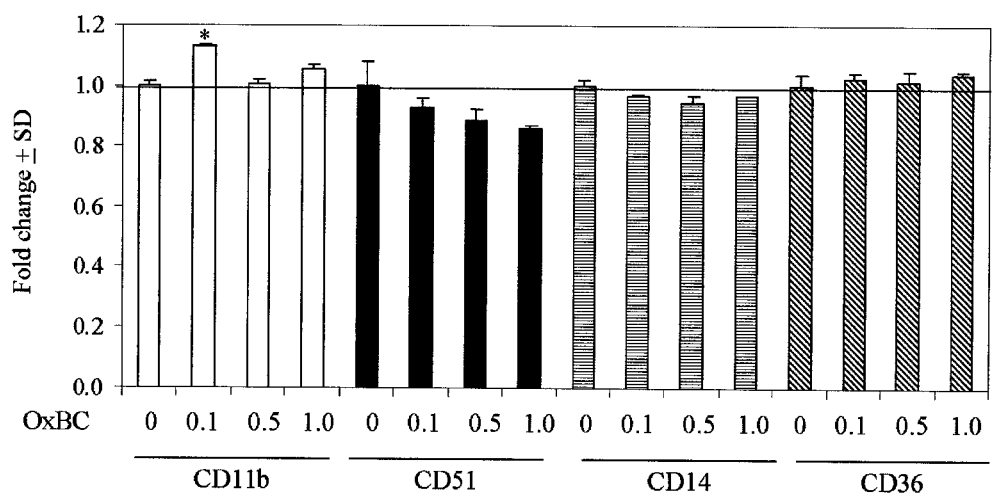
FIG. 5 is a graph depicting the differentiation antigen expression in THP-1 cells following OxBC treatment and LPS challenge. THP-1 monocytes were incubated with the indicated concentration of OxBC or DMSO control for 24 h and then challenged with 15 ng/ml of LPS five days later. Values represent fold changes relative to controls not treated with OxBC (* $p<0.02$, Student's t-test versus untreated control). Treatment of monocytes with lower concentrations of OxBC prior to challenge with LPS did not have a significant effect on expression of receptors involved in innate immunity.
Figure 6:
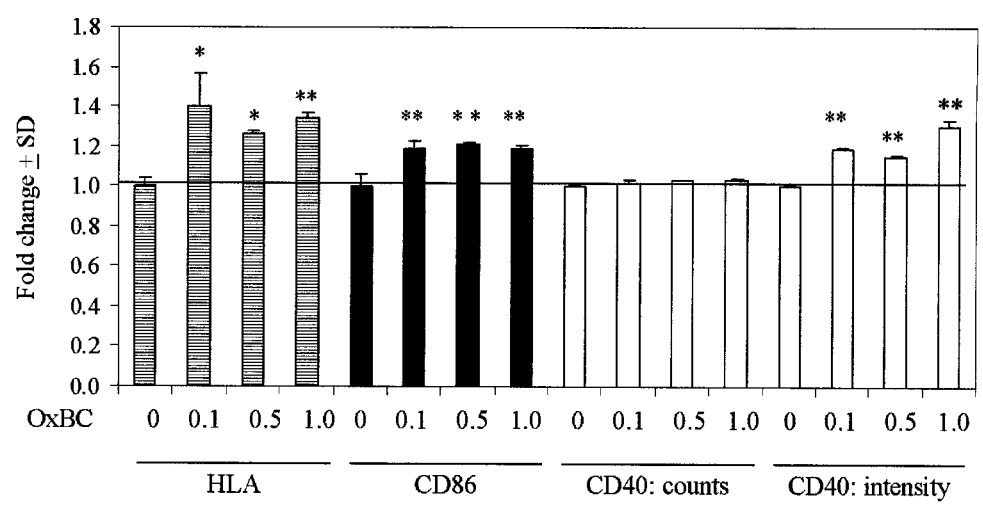
FIG. 6 is a graph depicting costimulatory molecule expression in THP-1 cells following OxBC treatment and LPS challenge. THP-1 monocytes were incubated with the indicated concentration of OxBC or DMSO control for 24 h and then challenged with 15 ng/ml of LPS five days later. Values represent fold changes relative to controls not treated with OxBC (* $p<0.05$,  $p<0.005$, * $p<0.001$, Student's t-test versus untreated control). Treatment with lower concentrations of OxBC tended to enhance the capacity of monocytes to participate in inducing an adaptive response to microbes.

We next evaluated receptor expression following treatment with lower concentrations of OxBC (≤1 μM) for 24 h and LPS challenge after approximately 5 days later. It should be noted that in the absence of LPS challenge, treatment of cells with these concentrations of OxBC did not effect expression of any of the receptors evaluated at the higher concentrations of the compound above (data not shown). Similarly, with the exception of CD11b expression at 0.1 no significant differences on the expression of differentiation antigens was observed between OxBC-treated and untreated cells following LPS stimulation (FIG. 5). In contrast, expression of costimulatory molecules involved in antigen presentation, namely HLA (DP/DR/DP) and CD86, was significantly elevated in OxBC-treated cultures compared to untreated controls following LPS challenge (FIG. 6). Similarly, although the preponderance of CD40 expression was not upregulated within the whole cell population by OxBC treatment, CD40 was expressed more abundantly in some subpopulations of OxBC treated cells compared to untreated controls. Thus, treatment with lower concentrations of OxBC appeared to enhance the capacity of monocytes to participate in inducing an adaptive response to microbes.

Example 3. Evaluation of the Phagocytosis Activity Exhibited by Oxidatively Transformed Carotenoid (OxBC)-Treated Human Monocytes The following results demonstrate that OxBC treatment is associated with increased phagocytosis. This study was designed to determine whether OxBC could influence phagocytotic activity in cultures of primary human monocyte and established THP-1 monocytoid cells. Increased phagocytosis was evident in naïve monocyte cultures treated with OxBC alone. However, the impact of OxBC was greatest in cultures pretreated with OxBC and then challenged with LPS. These results suggest that OxBC has the capacity to prime monocytes to respond to LPS challenge with increased phagocytic activity.

Phagocytosis is a fundamental mechanism of innate immune defense that serves as the classic model of microbe-innate immune interaction. To achieve this function, phagocytes express a broad spectrum of receptors that participate in particle recognition and internalization. Some of these receptors are capable of transmitting intracellular signals that trigger phagocytosis. However, others such as the scavenger receptors (eg. CD36) participate in binding to targets or act to increase the efficiency of internalization. A deceptively complex process, phagocyte-microbe contact requires an array of intracellular signals that trigger cellular processes as diverse as cytoskeletal rearrangement, alterations in membrane trafficking, activation of microbial killing mechanisms, production of pro- and anti-inflammatory cytokines and chemokines, activation of apoptosis, and production of molecules required for efficient antigen presentation to the adaptive immune system. Thus, phagocytosis is a process essential to both monocyte function and the regulation of innate antimicrobial defenses. The studies of Examples 1 and 2 demonstrate that OxBC possesses the ability to activate diverse innate responses in monocyte cultures. Given that many of these responses can be triggered by phagocytosis, we next evaluated the capacity for OxBC to influence phagocytic activity in monocytes.

Methods

Compound Preparation

OxBC stocks were prepared as described in Example 1.

Cell Lines and Conditions

Human THP-1 monocytoid cells (acute monocytic leukemia) were obtained from American Type Tissue Collection (#TIB-202). Cells were cultured in RPMI-1640 medium supplemented with 2 mM L-glutamine, 10 mM HEPES, 1.0 mM sodium pyruvate, 10% fetal bovine serum and antibiotics. Primary peripheral blood monocytes (PBM) were isolated from mixed peripheral blood mononuclear cell preparations using the Miltenyi Biotec MACs magnetic separation system. PBM were cultured in the same medium as THP-1 cells, with the exception that 20% fetal bovine serum was used. Cells were seeded ($1 \times 10^5$ cells/well, 96-well culture plates) 24 h prior to treatment with OxBC, PMA (25 ng/ml) and/or LPS (15 ng/ml) as described below. Cells incubated in an equivalent percentage (v/v) of DMSO alone served as controls.

Phagocytosis Assay

Phagocytosis in monocyte cultures was evaluated using a Vybrant phagocytosis assay kit (Invitrogen, #V6694) based upon the ingestion of fluorescein-labeled E. coli (strain K12) bacterial particles. Briefly, treated cells were incubated at 37° C. for 5 h with a 1000 suspension of fluorescent bioparticles in Hank's buffered salt solution. Following incubation, the suspension was removed and replaced with 100 μl of 2% trypan blue solution for 1 minute. The trypan blue solution was removed and the number of ingested particles determined using a fluorescence microplate reader (480 nm excitation, 520 nm emission). Wells containing only medium (no cells) served as negative reaction controls against which each experimental replicate was equalized. Three treatment scenarios were investigated for both THP-1 cells and PBM prior to determining phagocytotic activity: (1) Cells were simply treated with OxBC or PMA for 24 h; (2) Cells were treated with OxBC or PMA for 24 h, at which point the compounds were removed and the cells cultured for an additional 24 h in complete medium; and (3) Cells were treated with OxBC or PMA for 24 h, at which point the compounds were removed and the cells cultured for an additional 24 h in complete medium containing LPS. For THP-1 cells, an additional scenario was investigated in which cells were treated with OxBC or PMA for 24 h, at which point the compounds were removed and the cells allowed to recover for 72 h in complete medium. After recovery, the cells were treated with LPS for an 24 h before phagocytosis was measured.

Results and Discussion

Figure 7:
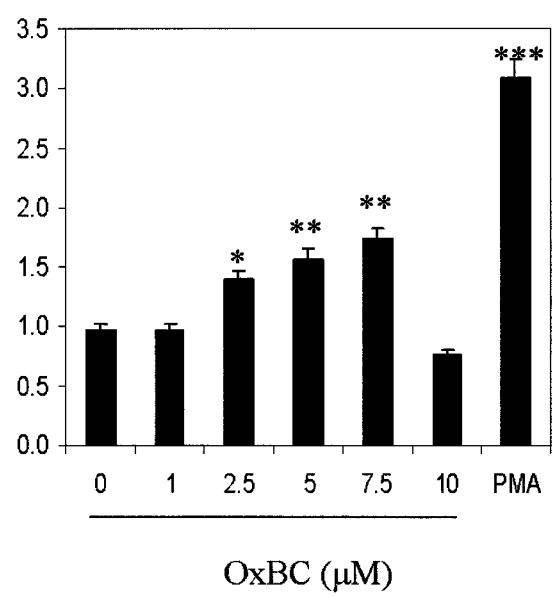
FIG. 7 is a graph depicting phagocytosis in OxBC treated THP-1 cells. THP-1 monocytes were incubated with the indicated concentration of OxBC or DMSO control for 24 h and then allowed to recover for 24 h in medium alone. Phagocytosis was evaluated after the recovery period. Values represent fold changes relative to controls. PMA was used at 25 ng/ml. * $p<0.05$,  $p<0.02$, * $p<0.002$, Student's t-test versus controls. OxBC significantly increased phagocytic activity in THP-1 cells suggesting increased antimicrobial activity.

The effect of OxBC on phagocytosis in monocytes was first evaluated in human THP-1 cells, an established monocytoid cell line, using concentrations and time courses that were previously shown not to result in significant toxicity. Treatment of naïve THP-1 cells with OxBC for 24 h did not significantly alter phagocytic activity at any of the concentrations evaluated. In contrast, PMA treatment was associated with a 12.94±2.05 fold increase in phagocytic activity relative to control cultures. However, OxBC treatment was found to influence phagocytic activity when THP-1 cells were allowed to recover for 24 h before phagocytosis was evaluated. Significantly increased phagocytic activity was observed in THP-1 cultures treated with 2.5, 5 or 7.5 µM (1.34, 2.67 or 4.02 µg/ml) of OxBC compared to controls, although this effect was approximately one-half that observed with PMA (see FIG. 7). Of note, OxBC at 10 µM (5.38 µg/ml) reduced the extent of phagocytosis in treated cultures, possibly due to toxic effects.

Figure 8:
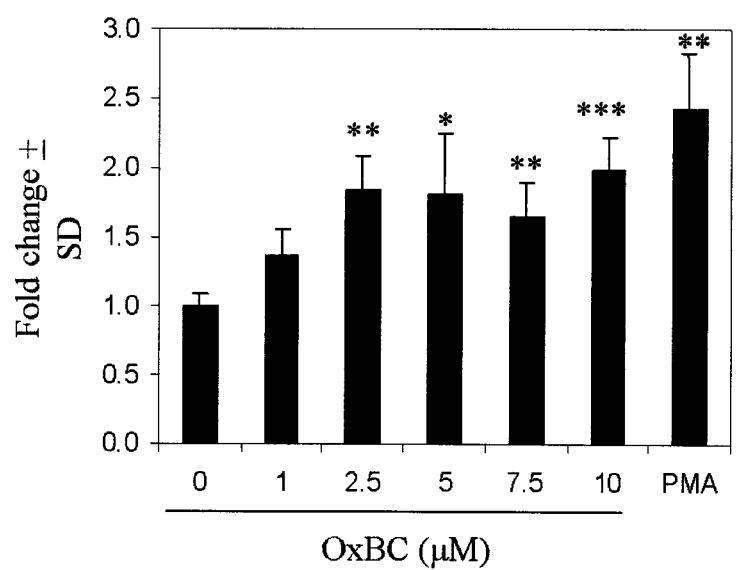
FIG. 8 is a graph depicting phagocytosis in OxBC-treated and LPS-stimulated THP-1 cells. THP-1 monocytes were incubated with the indicated concentration of OxBC or DMSO control for 24 h before being treated with LPS (15 ng/ml). Phagocytosis was evaluated 24 h after LPS stimulation. Values represent fold changes relative to controls. PMA was used at 25 ng/ml. * $p<0.05$,  $p<0.02$, * $p<0.002$, Student's t-test versus controls. THP-1 cells treated with OxBC exhibited greater phagocytic activity following challenge with LPS than untreated controls.

Examples 1 and 2 demonstrate that OxBC treatment can prime monocytes to enhance response to secondary stimuli, such as LPS. Consistent with these observations, THP-1 cells treated with OxBC exhibit greater phagocytic activity following LPS challenge than untreated controls (FIG. 8). Pretreatment with OxBC at concentrations exceeding 2.5 µM (1.34 µg/ml) increased phagocytosis to similar levels as that observed in monocytes treated with PMA.

Figure 9:
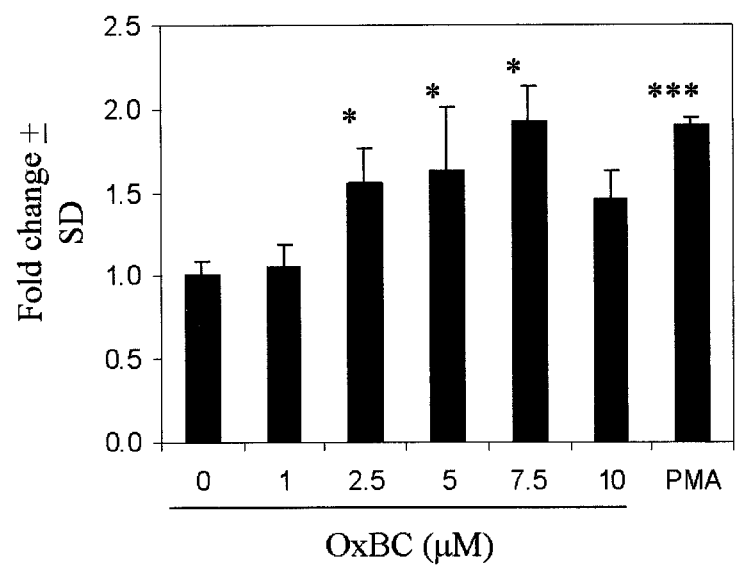
FIG. 9 is a graph depicting phagocytosis in OxBC-treated and LPS-stimulated primary PBM. Primary PBM were incubated with the indicated concentration of OxBC or DMSO control for 24 h before being treated with LPS (15 ng/ml). Phagocytosis was evaluated 24 h after LPS stimulation. Values represent fold changes relative to controls. PMA was used at 25 ng/ml. * $p<0.05$, *** $p<0.002$, Student's t-test versus controls. Primary human monocytes responded to OxBC treatment by increasing their phagocytic activity in response to LPS stimulation.

Similar results were observed when primary PBM were evaluated. When a regimen of 24 h treatment with OxBC followed by 24 h recovery was employed, a general increase in phagocytic activity of approximately 35% was detected in OxBC-treated cells relative to controls. Despite the observed increases, these results failed to reach statistical significance due to variability between replicates. Although increasing the number of replicates may have raised these responses to more significant levels by decreasing variability, this option was not viable due to the large number of primary cells that would be required. However, as with THP-1 cells, OxBC was found to prime PBM to respond to LPS challenge. As shown in FIG. 9, pretreatment with OxBC was associated with an increased phagocytic response to LPS stimulation that was comparable to that obtained with PMA at maximal levels.

Phagocytic activity was also evaluated in THP-1 cells that were allowed to recover for 72 h after OxBC treatment. Modest increases in phagocytosis were observed in cells treated with OxBC alone, although these responses were overshadowed by the large increase in phagocytic activity evident in PMA-treated cultures. In comparison, OxBC pretreatment was again found to prime THP-1 cells to respond to a LPS stimulus delivered 72 h later. Significantly increased phagocytic activity was detected in monocytes pretreated with OxBC at concentrations exceeding 5 µM (2.67 µg/ml), suggesting that the effects of OxBC treatment persist for several days after monocytes are first exposed to OxBC.

OxBC exhibits the capacity to directly increase the phagocytic activity of both primary and established monocytes. However, the greatest impact of OxBC on the immune system appears to be its ability to prime monocytes to respond to subsequent LPS challenge with a more intense phagocytic response.

OTHER EMBODIMENTS

All publications and patent applications, and patents mentioned in this specification are herein incorporated by reference.

While the invention has been described in connection with specific embodiments, it will be understood that it is capable of further modifications. Therefore, this application is intended to cover any variations, uses, or adaptations of the invention that follow, in general, the principles of the invention, including departures from the present disclosure that come within known or customary practice within the art.

Other embodiments are within the claims.

What we claim is:

1. A method of enhancing immune response in a subject having a bacterial infection, said method comprising administering to said subject a polymeric material in an amount of from 5 µg/kg to 50 mg/kg of body weight per day to enhance immune function in the subject, wherein said polymeric material is formed by reaction of 6 to 8 molar equivalents of oxygen with a carotenoid selected from β-carotene and lycopene, wherein said polymeric material has a molecular weight of greater than 1,000 Daltons.

2. The method of claim 1, wherein said polymeric material is administered intravenously, ocularly, intramuscularly, topically, subcutaneously, or intranasally.

3. The method of claim 1, wherein said bacterial infection is selected from the group consisting of community-acquired pneumonia, upper and lower respiratory tract infection, skin and soft tissue infection, acute bacterial otitis media, bacterial pneumonia, complicated infection, pyelonephritis, intra-abdominal infection, bacterial sepsis, central nervous system infection, bacteremia, wound infection, peritonitis, meningitis, infections after burn, urogenital tract infection, pelvic inflammatory disease, endocarditis, and intravascular infection.

4. The method of claim 1, wherein said polymeric material is administered ocularly for the treatment of an eye infection.

5. The method of claim 1, wherein said polymeric material is administered topically to the mouth of said subject for the treatment of an oral infection.

6. The method of claim 1, further comprising administering to said subject an antibiotic, wherein said polymeric material and said antibiotic are administered simultaneously, or within 14 days of each other.

7. The method of claim 6, wherein said antibiotic is selected from the group consisting of aminoglycosides, amphenicols, ansamycins, β-Lactams, carbapenems, cephalosporins, cephamycins, monobactams, oxacephems, lincosamides, macrolides, polypeptides, tetracyclines, 2,4-diaminopyrimidines, nitrofurans, quinolones, sulfonamides, sulfones, lipopeptides, and ketolides.

8. The method of claim 6, wherein said antibiotic is selected from the group consisting of amikacin, apramycin, arbekacin, bambermycins, butirosin, dibekacin, dihydrostreptomycin, fortimicin(s), fradiomycin, gentamicin, ispamicin, kanamycin, micronomicin, neomycin, neomycin undecylenate, netilmicin, paromomycin, ribostamycin, sisomicin, spectinomycin, streptomycin, streptonicozid, tobramycin, azidamfenicol, chloramphenicol, chloramphenicol palmitate, chloramphenicol pantothenate, florfenicol, thiamphenicol, rifampin, rifabutin, rifapentine, rifaximin, amidinocillin, amdinocillin, pivoxil, amoxicillin, ampicillin, aspoxicillin, azidocillin, azlocillin, bacampicillin, benzylpenicillinic acid, benzylpenicillin, carbenicillin, carfecillin, carindacillin, clometocillin, cloxacillin, cyclacillin, dicloxacillin, diphenicillin, epicillin, fenbenicillin, floxicillin, hetacillin, lenampicillin, metampicillin, methicillin, mezlocillin, nafcillin, oxacillin, penamecillin, penethamate hydriodide, penicillin G benethamine, penicillin G benzathine, penicillin G benzhydrylamine, penicillin G calcium, penicillin G hydragamine, penicillin G potassium, penicillin G, procaine, penicillin N, penicillin O, penicillin V, penicillin V benzathine, penicillin V hydrabamine, penimepicycline, phenethicillin, piperacillin, pivapicillin, propicillin, quinacillin, sulbenicillin, talampicillin, temocillin, ticarcillin, imipenem, 1-carba (dethia) cephalosporin, cefactor, cefadroxil, cefamandole, cefatrizine, cefazedone, cefazolin, cefixime, cefmenoxime, cefodizime, cefonicid, cefoperazone, ceforanide, cefotaxime, cefotiam, cefpimizole, cefpirimide, cefpodoxime proxetil, cefroxadine, cefsulodin, ceftazidime, cefteram, ceftezole, ceftibuten, ceftizoxime, ceftriaxone, cefuroxime, cefuzonam, cephacetrile sodium, cephalexin, cephaloglycin, cephaloridine, cephalosporin, cephalothin, cephapirin sodium, cephradine, pivcefalexin, cephalothin, cefaclor, cefotetan, cefprozil, loracarbef, cefetamet, cefepime, cefbuperazone, cefmetazole, cefminox, cefetan, cefoxitin, aztreonam, carumonam, tigemonan, flomoxef, moxolactam, clindamycin, lincomycin, azithromycin, carbomycin, clarithromycin, erythromycin(s) and derivatives, josamycin, leucomycins, midecamycins, miokamycin, oleandomycin, primycin, rokitamycin, rosaramicin, roxithromycin, spiramycin, troleandomycin, amphomycin, bacitracin, capreomycin, colistin, enduracidin, enylomycin, fusafungine, gramicidin(s), gramicidin S, mikamycin, polymyxin, polymyxin β-methanesulfonic acid, pristinamycin, ristocetin, teicoplanin, thiostrepton, tuberactinomycin, tyrocidine, tyrothricin, vancomycin, viomycin(s), virginiamycin, zinc bacitracin, spicycline, chlortetracycline, clornocycline, demeclocycline, doxycycline, guamecycline, lymecycline, meclocycline, methacycline, minocycline, oxytetracycline, penimepicycline, pipacycline, rolitetracycline, sancycline, senociclin, tetracycline, brodimoprim, tetroxoprim, trimethoprim, furaltadone, furazolium, nifuradene, nifuratel, nifurfoline, nifurpirinol, nifurprazine, nifurtoinol, nitrofurantoin, amifloxacin, cinoxacin, ciprofloxacin, difloxacin, enoxacin, fleroxacin, flumequine, lomefloxacin, miloxacin, nalidixic acid, norfloxacin, ofloxacin, oxolinic acid, perfloxacin, pipemidic acid, piromidic acid, rosoxacin, temafloxacin, tosufloxacin, acetyl sulfamethoxypyrazine, acetyl sulfisoxazole, azosulfamide, benzylsulfamide, chloramine-β, chloramine-T, dichloramine-T, formosulfathiazole, N2-formyl-sulfisomidine, N4-β-D-glucosylsulfanilamide, mafenide, 4'-(methyl-sulfamoyl)sulfanilanilide, p-nitrosulfathiazole, noprylsulfamide, phthalylsulfacetamide, phthalylsulfathiazole, salazosulfadimidine, succinylsulfathiazole, sulfabenzamide, sulfacetamide, sulfachlorpyridazine, sulfachrysoidine, sulfacytine, sulfadiazine, sulfadicramide, sulfadimethoxine, sulfadoxine, sulfaethidole, sulfaguanidine, sulfaguanol, sulfalene, sulfaloxic acid, sulfamerazine, sulfameter, sulfamethazine, sulfamethizole, sulfamethomidine, sulfamethoxazole, sulfamethoxypyridazine, sulfametrole, sulfamidochrysoidine, sulfamoxole, sulfanilamide, sulfanilamidomethanesulfonic acid triethanolamine salt, 4-sulfanilamidosalicyclic acid, N4-sulfanilylsulfanilamide, sulfanilylurea, N-sulfanilyl-3,4-xylamide, sulfanitran, sulfaperine, sulfaphenazole, sulfaproxyline, sulfapyrazine, sulfapyridine, sulfasomizole, sulfasymazine, sulfathiazole, sulfathiourea, sulfatolamide, sulfisomidine, sulfisoxazole, acedapsone, acediasulfone, acetosulfone, dapsone, diathymosulfone, glucosulfone, solasulfone, succisulfone, sulfanilic acid, p-sulfanilylbenzylamine, p,p'-sulfonyldianiline-N,N'digalactoside, sulfoxone, thiazolsulfone, daptomycin, linezolid, telithromycin, clofoctol, hexedine, magainins, methenamine, methenamine anhydromethylene-citrate, methenamine hippurate, methenamine mandelate, methenamine subsalicylate, nitroxoline, squalamine, xibomol, cycloserine, mupirocin, and tuberin.

9. The method of claim 1, wherein said subject is a domesticated pet.

10. The method of claim 9, wherein said domesticated pet is selected from the group consisting of a dog, cat, horse, and bird.

11. The method of claim 1, wherein said subject is an agricultural animal.

12. The method of claim 11, wherein said agricultural animal is selected from the group consisting of a sheep, swine, cow, turkey, chicken, or fish.

13. The method of claim 1, wherein said subject is a human.

14. The method of claim 1, wherein said polymeric material is formed by reaction of 6 to 8 molar equivalents of oxygen with β-carotene.

15. The method of claim 1, wherein enhancing immune function in the subject comprises increasing the expression of IL-8 in the subject.

16. The method of claim 1, wherein enhancing immune function in the subject comprises increasing the expression of MCP-1 in the subject.

17. The method of claim 1, wherein enhancing immune function in the subject comprises activating the innate immune system in the subject.

18. The method of claim 1, wherein enhancing immune function in the subject comprises activating the adaptive immune system in the subject.

19. The method of claim 1, wherein enhancing immune function in the subject comprises increasing phagocytotic activity in the subject.

* * * * *